US011597938B2

(12) United States Patent
Chomvong et al.

(10) Patent No.: US 11,597,938 B2
(45) Date of Patent: Mar. 7, 2023

(54) ENGINEERED MICROORGANISMS FOR ENHANCED USE OF OLIGOSACCHARIDES

(71) Applicant: Zimitech, Inc., Berkeley, CA (US)

(72) Inventors: Kulika Chomvong, Pathum Thani (TH); James Harrison Doudna Cate, Berkeley, CA (US); Yong-Su Jin, Champaign, IL (US)

(73) Assignee: Zimitech, Inc., Alameda, CA (US)

( * ) Notice: Subject to any disclaimer, the term of this patent is extended or adjusted under 35 U.S.C. 154(b) by 58 days.

(21) Appl. No.: 16/627,191

(22) PCT Filed: Jun. 29, 2018

(86) PCT No.: PCT/US2018/040351
§ 371 (c)(1),
(2) Date: Dec. 27, 2019

(87) PCT Pub. No.: WO2019/006341
PCT Pub. Date: Jan. 3, 2019

(65) Prior Publication Data
US 2020/0165621 A1  May 28, 2020

Related U.S. Application Data

(60) Provisional application No. 62/527,182, filed on Jun. 30, 2017.

(51) Int. Cl.
| *C12P 19/18* | (2006.01) |
| *C12N 1/19* | (2006.01) |
| *C12N 15/81* | (2006.01) |
| *C12N 9/10* | (2006.01) |
| *C12N 15/54* | (2006.01) |
| *C07K 14/395* | (2006.01) |
| *C12N 9/14* | (2006.01) |
| *C12P 19/00* | (2006.01) |

(52) U.S. Cl.
CPC ............ *C12N 15/81* (2013.01); *C07K 14/395* (2013.01); *C12N 9/14* (2013.01); *C12P 19/00* (2013.01); *C12Y 306/01003* (2013.01)

(58) Field of Classification Search
None
See application file for complete search history.

(56) References Cited

U.S. PATENT DOCUMENTS

| 8,431,360 B2 | 4/2013 | Glass et al. |
| 8,765,410 B2 | 7/2014 | Glass et al. |
| 9,012,177 B2 | 4/2015 | Glass et al. |
| 2010/0029693 A1 | 2/2010 | Douangpanya et al. |
| 2011/0159560 A1 | 6/2011 | Donaldson et al. |
| 2014/0057323 A1* | 2/2014 | Doudna Cate ............... C12Y 302/01021 435/97 |
| 2017/0152538 A1* | 6/2017 | Lee ................. C12Y 204/01069 |
| 2020/0165621 A1 | 5/2020 | Chomvong et al. |

FOREIGN PATENT DOCUMENTS

| EP | 2927316 A1 | 10/2015 |
| WO | WO-2008/124162 A2 | 10/2008 |
| WO | WO-2010/111344 A2 | 9/2010 |
| WO | WO-2014/022692 A1 | 2/2014 |
| WO | WO-2019/006341 A1 | 1/2019 |

OTHER PUBLICATIONS

Guo et al., Comp. Struct. Biotechnol. J. 15:161-167, 2017 (Year: 2017).*
Pathanibul, P., "Production of a Functional Human Milk Oligosaccharide, 2'-Fucosyllactose, Using Microbial Cell Factories", Dissertation, University of Illinois at Urbana-Champain, 2015 (Year: 2015).*
Zhou et al., Cell Mol Life Sci 63:2260-2290, 2006 (Year: 2006).*
Kozak, M., Gene 234:187-208, 1999 (Year: 1999).*
Chin et al., J. Biotechnol. 210:107-115, 2015 (Year: 2015).*
Lim, H., "Metabolic engineering of *Saccharomyces cerevisiae* for efficient production of 2'-fucosyllactose", Dissertation, University of Illinois, Urbana-Champaign, 2017 (Year: 2017).*
Kayikci et al., FEMS Yeast Res. 15:fov068, 2015, 8 pages (Year: 2015).*
Guimaraes et al., Biotechnol. Adv. 28:375-384, 2010 (Year: 2010).*
Chomvong et al., "ATP Homeostasis Underlies Optimal Glucose Consumption by *Saccharomyces cerevisiae*," bioRxiv, pp. 1-41 (2016).
Davis et al., "The ATP binding site of the yeast plasma membrane proton-translocating ATPase," *Journal of Biological Chemistry*, 265(3):1300-1305 (1990).
International Search Report and Written Opinion International Application PCT/US18/40351 dated Nov. 30, 2018.
Partial Supplementary European Search Report for EP Application No. EP 18823720 dated Mar. 10, 2021.
Extended European Search Report for EP Application No. 18823720.0 dated Sep. 30, 2021.

(Continued)

*Primary Examiner* — David Steadman
(74) *Attorney, Agent, or Firm* — Foley Hoag LLP; Lucas P. Watkins; Mohanad Mossalam

(57) ABSTRACT

Disclosed herein are genetically modified microorganisms and related methods for enhanced utilization of oligosaccharides and improved productivity of compounds derived from the metabolism of the oligosaccharides. The microorganisms described herein have altered activities of plasma membrane ATPase protein (PMA1) and/or one or more extracellular glucose sensors, namely, sucrose non-fermenting protein (SNF3), restores glucose transport protein (RGT2), and G protein-coupled receptor 1 protein (GPR1). These genetic modifications provide the microorganisms an increased ability to utilize an oligosaccharide to produce a compound of interest, particularly, tagatose, 2'-fucosyllactose, and psicose. Methods of culturing the microorganisms in the presence of such oligosaccharides to produce the products of interest are also provided.

11 Claims, 9 Drawing Sheets

Specification includes a Sequence Listing.

(56) References Cited

OTHER PUBLICATIONS

Jiang et al., "Two Glucose Sensing/Signaling Pathways Stimulate Glucose-induced Inactivation of Maltose Permease in *Saccharomyces*," Molecular Biology of the Cell, 8: 1293-1304 (1997).

Lee et al., "Overexpression of PMA1 enhances tolerance to various types of stress and constitutively activates the SAPK pathways in *Saccharomyces cerevisiae*," Applied Microbiology and Biotechnology, 101: 229-239 (2017).

Lemaire et al., "Glucose and Sucrose Act as Agonist and Mannose as Antagonist Ligands of the G Protein-Coupled Receptor Gpr1 in the Yeast *Saccharomyces cerevisiae*," Molecular Cell, 16(22): 293-299 (2004).

Liang et al., "A Novel Signal Transduction Pathway in *Saccharomyces cerevisiae* Defined by Snf3-regulated Expression of HXT6," Molecular Biology of the Cell, 7: 1953-1966 (1996).

Rodriguez et al., "Glucose Signaling in Yeast Is Partially Mimicked by Galactose and Does Not Require the Tps1 Protein," Molecular Cell Biology Research Communications, 1:52-58 (1999).

Roy et al., "The Glucose Signal Transduction Pathway Mediated by the Rgt2 and Snf3 Glucose Sensors in the Budding Yeast," Microbiology India M.Sc. in Microbiology: 154 pages (2014).

Baumgärtner et al., "Galactose-limited fed-batch cultivation of *Escherichia coli* for the production of lacto-N-tetraose," Enzyme and Microbial Technology, 75-76: 37-43 (2015).

Baumgärtner et al., "Synthesis of the Human Milk Oligosaccharide Lacto-N-tetraose in Metabolically Engineered, Plasmid-Free *E. coli*," ChemBioChem, 15:1896-1900 (2014).

Huang et al, "Metabolic engineering of *Escherichia coli* for the production of 2'-fucosyllactose and 3-fucosyllactose through modular pathway enhancement," Metabolic Engineering, Author's Accepted Manuscript: 62 pages (2017).

Priem et al., "A new fermentation process allows large-scale production of human milk oligosaccharides by metabolically engineered bacteria," Glycobiology, 12(4): 235-240 (2002).

Soo-Han et al., "Biotechnological production of human milk oligosaccharides," Biotechnology Advances, 30: 1268-1278 (2012).

Choi et al., "Disruption of Snf3/Rgt2 glucose sensors decreases lifespan and caloric restriction effectiveness through Mth1/Std1 by adjusting mitochondrial efficiency in yeast," FEBS Letters, 589: 349-357 (2015).

\* cited by examiner

Fig. 5

```
  1 mtdtssssss ssassvsahq ptqekpakty ddaasessdd ddidalieel qsnhgvdded
 61 sdndgpvaag earpvpeeyl qtdpsyglts devlkrrkky glnqmadeke slvvkfvmff
121 vgpiqfvmea aailaaglsd wvdfgvicgl lmlnagvgfv qefqagsivd elkktlanta
181 vvirdgqlve ipanevvpgd ilqledgtvi ptdgrivted cflqidqsai tgeslavdkh
241 ygdqtfssst vkrgegfmvv tatgdntfvg raaalvnkaa ggqghftevl ngigiillvl
301 viatlllvwt acfyrtngiv rilrytlgit iigvpvglpa vvtttmavga aylakkqaiv
361 qklsaiesla gveilcsdkt gtltknklsl hepytvegvs pddlmltacl aasrkkkgld
421 aidkaflksl kqypkakdal tkykvlefhp fdpvskkvta vvespegeri vcvkgaplfv
481 lktveedhpi pedvhenyen kvaelasrgf ralgvarkrg eghweilgvm pcmdpprddt
541 aqtvsearhl glrvkmltgd avgiaketcr qlglgtniyn aerlglgggg dmpgseladf
601 venadgfaev fpqhkyrvve ilqnrgylva mtgdgvndap slkkadtgia vegatdaars
661 aadivflapg lsaiidalkt srqifhrmys yvvyrialsl hleiflglwi aildnsldid
721 livfiaifad vatlaiaydn apyspkpvkw nlprlwgmsi ilgivlaigs witlttmflp
781 kggiiqnfga mngimflqis ltenwlifit raagpfwssi pswqlagavf avdiiatmft
841 lfgwwsenwt divtvvrvwi wsigifcvlg gfyyemstse afdrlmngkp mkekkstrsv
901 edfmaamqrv stqheket
```

Fig. 6

```
  1 mdpnsnssse tlrqekqgfl dkalqrvkgi alrrnnsnkd httddttgsi rtptslqrqn
 61 sdrqsnmtsv ftddistidd nsilfseppq kqsmmmsicv gvfvavggfl fgydtglins
121 itsmnyvksh vapnhdsfta qqmsilvsfl slgtffgalt apfisdsygr kptiifstif
181 ifsignslqv gaggitlliv grvisgigig aisavvplyq aeathkslrg aiistyqwai
241 twgllvssav sqgtharnda ssyripiglq yvwssflaig mfflpespry yvlkdkldea
301 akslsflrgv pvhdsgllee lveikatydy easfgssnfi dcfissksrp kqtlrmftgi
361 alqafqqfsg infifyygvn ffnktgvsns ylvsfityav nvvfnvpglf fveffgrrkv
421 lvvggvimti anfivaivgc slktvaaakv miaficlfia afsatwggvv wvisaelypl
481 gvrskctaic aaanwlvnfi calitpyivd tgshtsslga kiffiwgsln amgvivvylt
541 vyetkgltle eidelyikss tgvvspkfnk direralkfq ydplqrledg kntfvakrnn
601 fddetprndf rntisgeidh spnqkevhsi pervdiptst eilespnkss gmtvpvspsl
661 qdvpipqtte paeirtkyvd lgnglglnty nrgppslssd ssedytedei ggpssqgdqs
721 nrstmndind ymarlihsts tasnttdkfs gnqstlryht asshsdttee dsnlmdlgng
781 lalnaynrgp psilmnssde eanggetsdn lntaqdlagm kermaqfaqs yidkrgglep
841 etqsnilsts lsvmadtneh nneilhssee natnqpvnen ndlk
```

Fig. 7

```
  1 mndsqnclrq reenshlnpg ndfghhqgae ctinhnnmph rnaytestnd teaksivmcd
 61 dpnayqisyt nnepagdgai ettsillsqp lplrsnvmsv lvgifvavgg flfgydtgli
121 nsitdmpyvk tyiapnhsyf ttsqiailvs flslgtffga liapyisdsy grkptimfst
181 avifsignsl qvasgglvll ivgrvisgig igiisavvpl yqaeaaqknl rgaiissyqw
241 aitigllvss avsqgthskn gpssyripig lqyvwssila vgmiflpesp ryyvlkdeln
301 kaakslsflr glpiedprll eelveikaty dyeasfgpst lldcfktsen rpkqilrift
361 giaiqafqqa sginfifyyg vnffnntgvd nsylvsfisy avnvafsipg mylvdrigrr
421 pvllaggvim aianlviaiv gvsegktvva skimiaficl fiaafsatwg gvvwvvsael
481 yplgvrskct aicaaanwlv nftcalitpy ivdvgshtss mgpkiffiwg glnvvavivv
541 yfavyetrgl tleeidelfr kapnsvissk wnkkirkrcl afpisqqiem ktniknagkl
601 dnnnspivqd dshniidvdg flenqiqsnd hmiaadkgsg slvniidtap ltstefkpve
661 hppvnyvdlg nglglntynr gppsiisdst defyeendss yynnnterng ansvntymaq
721 linsssttsn dtsfspshns nartssnwts dlaskhsqyt spq
```

Fig. 8

```
  1 mitegfppnl nalkgsslle krvdslrqln tttvnqllgl pgmtstftap qllqlriiai
 61 tasavsliag clgmfflskm dkrrkvfrhd liafliicdf lkafilmiyp miilinnsvy
121 atpaffntlg wftafaiega dmaimifaih failifkpnw kwrnkrsgnm egglykkrsy
181 iwpitalvpa ilaslafiny nklnddsdtt iildnnnynf pdsprqggyk pwsawcylpp
241 kpywykivls wgpryfiiif ifavylsiyi fitseskrik aqigdfnhnv leeekekkkl
301 fglghwgkak wyfrsyfklp llhllrnlkn fftisfidpn eetddsgssn gtfnfgessn
361 eiptlfrktn tgsdenvsas ggvrlldyns akpldmskya mseqpdlern npfdcendit
421 lnpselvskq kehkvtfsve negldtrkss mlghqtfscq nslesplamy dnkndnsdit
481 snikekggii nnnsnndddd nnnnndndnd nnnsnnnnnn nnnnnnnnnn nnnnnnnnnn
541 nnnnsnnikn nvdnnntnpa dniptlsnea ftpsqqfsqe rvnnnadrce nssftnvqqh
601 fqaqtykqmk krraqiqknl raifiyplsy igiwlfpiia dalqynheik hgptmwvtyi
661 dtcvrplscl vdvivylfke kpwnyswakt eskyliekyi lkgelgekei lkfchsnwgk
721 rgwyyrgkwk krkcwkystn plkrilwfve rffkqlfelk lhfsfydncd dfeywenyys
781 akdsndnkrt esdetktnss drslpsnsle lqamlnnita eevevplfwr iihhipmlgg
841 idldelnrll kirynndhfs lpglkfalnq nkshdkhqdv stnsmvkssf fssnivtndd
901 ensieedknl rysdasasen ylvkptipgt tpdpiieaqn dndssdssgi dliaflrngp
961 l
```

ENGINEERED MICROORGANISMS FOR ENHANCED USE OF OLIGOSACCHARIDES

RELATED APPLICATIONS

This application is a national-stage application of International Application No. PCT/US2018/40351, filed Jun. 29, 2018, which claims priority to U.S. Provisional Application No. 62/527,182, filed Jun. 30, 2017, the contents of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 27, 2018, is named ZTW-00125_SL.txt and is 30,584 bytes in size.

BACKGROUND

Oligosaccharides are low molecular weight carbohydrates, containing sugar moieties with a degree of polymerization (DP) between 2 and 10. Oligosaccharides may be obtained from natural sources and may also be synthesized. Some microorganisms naturally consume oligosaccharides and utilize oligosaccharides as their energy sources. Various natural sources of oligosaccharides include milk, honey, sugarcane juice, rye, barley, wheat, soybean, lentils, mustard, fruits, and vegetables such as onion, asparagus, sugar beet, artichoke, chicory, leek, garlic, banana, yacon, tomato, and bamboo shoots. Common oligosaccharide manufacturing methods include hydrolysis of polysaccharides, chemical, and enzymatic polymerization from disaccharide or monosaccharide substrates. Acid, alkali, and enzymatic hydrolysis of polysaccharides generates oligosaccharides of desired structure and functional properties. In general, enzymatic methods are preferred for oligosaccharide synthesis due to their high selectivity and yields, and environmental-friendly nature. Other oligosaccharides may be engineered by introducing exogenous genes to enable oligosaccharides consumption.

Functional oligosaccharides have emerged as valuable components of food and dietary supplements. Their resistance to digestion and fermentation by colonic microbes has given oligosaccharides a nutritional edge. Apart from implications as dietary fibers, sweeteners, and humectants, they are hailed as prebiotics. Their beneficial effects extend from anti-oxidant, anti-inflammatory, immunomodulatory, anti-hypertensive, and anti-allergic to anti-cancer, neuroprotective, and improvement of the skin barrier function and hydration. The rising popularity of bioactive oligosaccharides has accelerated the search for their generation from new, sustainable sources.

Oligosaccharides are frequently used as a carbon source or feedstock to fuel the fermentation or other metabolic processes in genetically modified microorganisms used to produce desired products. However, the efficiency of this process is limited by the genetically modified microorganism's ability to efficiently utilize the carbon source provided. In addition, all natural and conventional genetically engineered oligosaccharide utilization systems lose energy during transport of the oligosaccharides into the microorganisms or during cleavage of the oligosaccharides. This loss of energy reduces the efficiency of the microorganism's production of chemicals, which in turn increases the cost and time of production. Therefore, compositions and methods for optimizing a microorganism's utilization of oligosaccharides to reduce the time and expense of producing chemicals is desired.

SUMMARY OF THE INVENTION

Microorganisms that exhibit increased utilization of oligosaccharides are provided. In certain embodiments, the microorganisms comprise one or more genetic modifications that: i) increase the activity of plasma membrane ATPase protein (PMA1), and/or ii) decrease the activity of sucrose non-fermenting protein (SNF3), and/or iii) decrease the activity of restores glucose transport protein (RGT2), and/or iv) decrease the activity of G protein-coupled receptor 1 protein (GPR1). In certain embodiments, these genetic modifications that result in i), ii), iii) and iv) are produced in plasma membrane ATPase gene (Pma1), sucrose non-fermenting gene (Snf3), glucose transport gene (Rgt2), and G protein-coupled receptor 1 gene (Gpr1), respectively.

Compared to the parental microorganisms, the microorganisms described herein have an increased ability to utilize oligosaccharides to produce products of interest from the metabolism of those oligosaccharides. Accordingly, methods of producing products of interest by culturing the microorganisms of the present disclosure in media containing the oligosaccharides and obtaining the products of interest from the media are provided.

In some embodiments, the microorganisms are bacteria or fungi, for example, filamentous fungi or yeasts. In specific embodiments, the microorganisms are yeast, for example, *Saccharomyces cerevisiae*.

BRIEF DESCRIPTION OF THE DRAWINGS

FIG. 5 shows the sequence of SEQ ID NO. 1.
FIG. 6 shows the sequence of SEQ ID NO. 2.
FIG. 7 shows the sequence of SEQ ID NO. 3.
FIG. 8 shows the sequence of SEQ ID NO. 4.

DETAILED DESCRIPTION

Definitions

Figure 1:
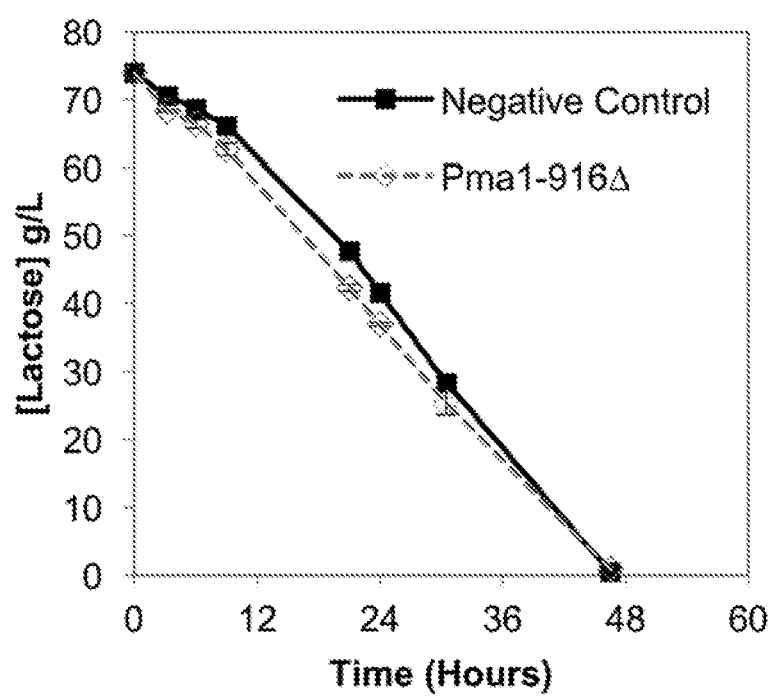
FIG. 1 shows that the introduction of constitutively active Pma1 improves oligosaccharides utilization in the absence of extracellular glucose.

For convenience, certain terms employed in the specification, examples, and appended claims are collected here.

As used herein, the singular forms "a," "an" and "the" are intended to include the plural forms as well, unless the context clearly indicates otherwise.

The term "about" means within an acceptable error range for the particular value as determined by one of ordinary skill in the art, which will depend in part on how the value is measured or determined, i.e., the limitations of the measurement system. Where the terms "about" or "approximately" are used in the context of compositions containing amounts of ingredients or conditions such as temperature, these values include the stated value with a variation of 0-10% around the value (X±10%).

The terms "including," "includes," "having," "has," "with," or variants thereof are inclusive in a manner similar to the term "comprising." The term "consisting" and the grammatical variations of consist encompass embodiments with only the listed elements and excluding any other elements. The phrases "consisting essentially of" or "consists essentially of" encompass embodiments containing the specified materials or steps and those including materials and steps that do not materially affect the basic and novel characteristic(s) of the embodiments.

Ranges are stated in shorthand to avoid having to set out at length and describe each and every value within the range. Therefore, when ranges are stated for a value, any appropriate value within the range can be selected, and these values include the upper value and the lower value of the range. For example, a range of two to thirty represents the terminal values of two and thirty, as well as the intermediate values between two to thirty, and all intermediate ranges encompassed within two to thirty, such as two to five, two to eight, two to ten, etc.

The term "genetic modification" as used herein refers to altering the genomic DNA in a microorganism. Typically, a genetic modification alters the expression and/or activity of a protein encoded by the altered gene.

The term "oligosaccharide" refers to monosaccharide polymers of varying length and includes: sucrose (1 glucose monomer and 1 fructose monomer), lactose (1 glucose monomer and 1 galactose monomer), maltose (1 glucose monomer and 1 glucose monomer), isomaltose (2 glucose monomers), isomaltulose (1 glucose monomer and 1 fructose monomer), trehalose (2 glucose monomers), trehalulose (1 glucose monomer and 1 fructose monomer) cellobiose (2 glucose monomers), cellotriose (3 glucose monomers), cellotetraose (4 glucose monomers), cellopentaose (5 glucose monomers), and cellohexaose (6 glucose monomers).

The term "microorganism" refers to prokaryote or eukaryote microorganisms capable of oligosaccharides consumption or utilization with or without modifications.

The term, "enhanced utilization" refers to an improvement in oligosaccharide consumption by a microorganism compared to a parental microorganism, specifically an increase in the oligosaccharides consumption rate, a decrease in the initial time before oligosaccharides consumption begins, an increase in the yield, defined as the ratio of product made to the starting material consumed, and/or a decrease in an overall time the microorganisms take to consume a given amount of an oligosaccharide.

The term "parental microorganism" refers to a microorganism that is manipulated to produce a genetically modified microorganism. For example, if a gene is mutated in a microorganism by one or more genetic modifications, the microorganism being modified is a parental microorganism of the microorganism carrying the one or more genetic modifications.

The term, "consumption rate" refers to an amount of oligosaccharides consumed by the microorganisms having a given cell density in a given culture volume in a given time period.

The term, "desired compounds" refer to compounds generated from the oligosaccharides by the microorganisms with or without modifications. Modifications other than those required to enable oligosaccharides consumption may be required for a production of the desired compounds. The desired compounds include tagatose, 2'-fucosyllactose, human milk oligosaccharides and, psicose.

The term, "production rate" refers to an amount of desired compounds produced by the microorganisms having a given cell density in a given culture volume in a given time period.

The term "gene" includes the coding region of the gene as well as the upstream and downstream regulatory regions. The upstream regulatory region is called the promoter region of the gene. The downstream regulatory region is called the terminator region. A gene is represented herein in small caps and italicized format of the name of the gene, whereas, a protein is represented in all caps and non-italicized format of the name of the protein. For example, pma1 (italicized) represents a gene encoding PMA1 protein; whereas, PMA1 (non-italicized and all caps) represents PMA1 protein.

The sequence identity of at least 60%, 65%, 70%, 75%, 80%, 85%, 90%, 95%, 96%, 97%, 98%, 99% or 100% to a reference sequence refers to a comparison made between two sequences using algorithms known in the art, such as the BLAST algorithm.

A "variant" is a gene or protein sequence deviates from a reference gene or protein. The terms "isoform," "isotype," and "analog" also refer to "variant" forms of a gene or a protein. The variant may have "conservative" changes, wherein a substituted amino acid has similar structural or chemical properties, e.g., replacement of leucine with isoleucine. A variant may have "non-conservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art.

"Exogenous nucleic acid" refers to a nucleic acid, DNA, or RNA, which has been artificially introduced into a cell. Such exogenous nucleic acid may or may not be a copy of a sequence or fragments thereof which is naturally found in the cell into which it was introduced.

"Endogenous nucleic acid" refers to a nucleic acid, gene, polynucleotide, DNA, RNA, mRNA, or cDNA molecule that is naturally present in a microorganism. An endogenous sequence is "native" to, i.e., indigenous to, the microorganism.

The term "mutation" refers to genetic modification to a gene including modifications to the open reading frame, upstream regulatory region, and downstream regulatory region.

A heterologous host cell for a nucleic acid sequence refers to a cell that does not naturally contain the nucleic acid sequence.

A "chimeric nucleic acid" comprises a first nucleotide sequence linked to a second nucleotide sequence, wherein the second nucleotide sequence is different from the sequence which is associated with the first nucleotide sequence in cells in which the first nucleotide sequence occurs naturally.

A constitutive promoter expresses an operably linked gene when RNA polymerase holoenzyme is available. Expression of a gene under the control of a constitutive promoter does not depend on the presence of an inducer.

An inducible promoter expresses an operably linked gene only in the presence of an inducer. An inducer activates the transcription machinery that induces the expression of a gene operably linked to an inducible promoter.

In certain aspects, disclosed herein are genetically engineered microorganisms capable of converting oligosaccharides into products of interest. For example, the microorganisms described herein can convert lactose into tagatose or Human Milk Oligosaccharides (HMO), such as 2'-fucosyllactose (2-FL) and lacto-N-tetraose (LNT), or convert sucrose into psicose. Also disclosed herein are methods for producing products of interest by culturing the microorganisms described herein in the presence of appropriate oligosaccharides and recovering the products of interest.

Certain embodiments of the present disclosure provide microorganisms comprising one or more genetic modifications selected from:

i) a genetic modification that increases the activity of PMA1 in the microorganism compared to PMA1 activity in the parental microorganism, ii) a genetic modification that decreases the activity of SNF3 in the microorganism compared to SNF3 activity in the parental microorganism, iii) a genetic modification that decreases the activity of RGT2 in the microorganism compared to RGT2 activity in the parental microorganism, and iv) a genetic modification that decreases the activity of GPR1 in the microorganism compared to GPR1 activity in the parental microorganism.

In particular embodiments, i) the genetic modification that increases the activity of PMA1 is a genetic modification to plasma membrane ATPase gene (pma1), ii) the genetic modification that decreases the activity of SNF3 is a genetic modification to sucrose non-fermenting gene (snf3), iii) the genetic modification that decreases the activity of RGT2 is a genetic modification to glucose transport gene (rgt2), and iv) the genetic modification that decreases the activity of GPR1 is a genetic modification to G protein-coupled receptor 1 gene (gpr1).

An example of PMA1 is provided by the sequence of SEQ ID NO: 1, which is PMA1 from *Saccharomyces cerevisiae*. Homologs of PMA1 from microorganisms other than *S. cerevisiae*, particularly, from yeast, can be used in the microorganisms and methods of the present disclosure. Non-limiting examples of the homologs of PMA1 useful in the instant disclosure are represented by Uniprot entries: A0A1U819G6, A0A1U8H4C1, A0A093V076, A0A1U8FCY1, Q08435, A0A1U7Y482, A0A1U8GLU7, P22180, A0A1U8G6C0, A0A1U8IAV5, A0A1U8FQ89, P09627, A0A199VNH3, P05030, P28877, A0A1U8I3U0, Q0EXL8, A0A1U8I3V7, P49380, Q07421, A0A1D8PJ01, P54211, P37367, P07038, Q0Q5F2, G8BGS3, A0A167F957, M5ENE2, A0A1B8GQT5, O74242, Q9GV97, Q6VAU4, A0A177AKN9, A0A1J6KB29, A0A2H9ZYJ6, A0A251UIM1, A0A251USM2, D2DVW3, M5BX73, Q6FXU5, A3LP36, G3ARI4, 9NSP9, A0A167C712, G2WE85, F2QNM0, A6ZUY5, C7GK65, A0A142GRJ4, W0T7K4, B3LDT4, A0A0H5BY16, A0A1B2J5T9, E7DB83, Q9UR20, F4NA03, Q96TH7, F4NA02, I2G7P2, C4PGL3, F4NA00, F4N9Z6, Q7Z8B7, F4N9Z9, A0A1L4AAP4, O94195, A0A1D1YKT6, A0A0U1YLR0, A0A0F8DBR8, A0A1C7N6N1, A0A2N6P2L5, A0A2C5WY03, O14437, T1VYW7, T1VY71, A1KAB0, C0QE12, K0NAG7, A0A0H3J1I1, A0A1Q9D817, A0A068MZP7, D1JED6, A0A2K8WRE9, A0A1A8YFD7, A0A1A8YG89, I2G7P8, D9PN36, D1JI19, B6IUJ9, B1XP54, H8W7G4, H6SL18, G8LCW3, L8AJP6, Q5ZFR6, A0A1D7QSR3, A0A1Q2TYG8, F4N054, A0A1Q9CTB2, A0A1Q9EJV5, A0A1D1XEE3, A0A0F7GAE0, D2DVW4, A0A0A9YX23, A0A1Q9ELW6. The Uniprot entries listed herein are incorporated by reference in their entireties.

Additional homologs of PMA1 are known in the art and such embodiments are within the purview of the present disclosure. For example, the homologs of PMA1 have at least 60%, 65%, 70%, 75%, 80%, 85%, 90%, 95%, or 99% sequence identity to SEQ ID NO: 1.

An example of SNF3 is provided by the sequence of SEQ ID NO: 2, which is SNF3 from *S. cerevisiae*. Homologs of SNF3 from microorganisms other than *S. cerevisiae*, particularly, from yeast, can be used in the microorganisms and methods of the present disclosure. Non-limiting examples of the homologs of SNF3 useful in the instant disclosure are represented by Uniprot entries: W0TFH8, Q6FNU3, A0A0W0CEX1, G2WBX2, A6ZXD8, J6EGX9, P10870, C7GV56, B3LH76, A0A0L8RL87, A0A0K3C9L0, M7WSX8, A0A1U8HEQ5, G5EBN9, A8X3G5, A3LZS0, G3AQ67, A0A1E4RGT4, A0A1B2J9B3, F2QP27, E3MDL0, A0A2C5X045, G0NWE1, A0A0H5S3Z1, A0A2G5VCG9, A0A167ER19, A0A167DDU9, A0A167CY60, A0A167CEW8, A0A167ER43, A0A167F8X4, A0A1B8GC68, A0A177A9B0, E3EIS7, E3E8B6, A0A0A9Z0Q2. The Uniprot entries listed herein are incorporated by reference in their entireties.

Additional homologs of SNF3 are known in the art and such embodiments are within the purview of the present disclosure. For example, the homologs of SNF3 have at least 60%, 65%, 70%, 75%, 80%, 85%, 90%, 95%, or 99% sequence identity to SEQ ID NO: 2.

An example of RGT2 is provided by the sequence of SEQ ID NO: 3, which is RGT2 from *S. cerevisiae*. Homologs of RGT2 from organisms other than *S. cerevisiae*, particularly, from yeast, can be used in the microorganisms and methods of the present disclosure. Non-limiting examples of the homologs of RGT2 are represented by Uniprot entries: A0A0U1MAJ7, N4TG48, A0A1Q8RPY1, N4U710, A0A1L7SSQ2, A0A1L7VB15, A0A0C4E497, A0A1L7UAN6, A0A0J0CU17, A0A1L7VMA9, S0ED22, A0A1L7SD48, N1R8L8, A0A1L7V0N4, S3BYD3, E4UUU6, N4UPT5, N4U030, A0A0I9YK83, S0DJS4, A0A0U1LWH9, A0A0K6FSJ2, N1S6K7, A0A0J6F3E5, A0A1E4RS51, N4UTN2, A0A0G2E6D5, A0A1J9R914, A0A0F4GQX7, A0A1S9RLB9, A3M0N3, J9PF54, A0A074WC52, A0A0K6GI66, N1QHS4, G2WXK0, B2VVL4, B2WDK7, A0A1J9S6A1, G4N0E9, L7JEU7, L7INA5, A0A0L1HE99, A0A0J8QL36, A0A0H5CKW2, A0A0J6Y4E2, W0VMG0, G2WQD8, A0A1C1WV61, A0A1S9RL33, C9SBA9, A0A0G2HY75, J3P244, N1QK04, A0A0N0NQR9, A0A1S7UJ19, G2XFE7, C9SWZ3, R8BUY9, M7SYH1, A0A1E1MIV2, A0A1E1LLK3, A0A1E1LJE1, L7J4Y3, L71304, A0A1L7XU29, A0A136JCY3, A0A0J8RG81, A0A177DW33, A0A1L7X792, W9C8U1, B2VXL1, A0A0L1HMG8, A0A178DQW4, A0A167V6F7, A0A166WR60, A0A162KLT6, A0A1L7X3D1, G3JQX8, Q7S9U8, E9F7A6, A0A1S7HPX9, A0A0G2G564, A0A0W0D0B3, A6ZXI9, Q12300, C7GKZ0, G2WC23, A0A0H5CAT9, J4U3Y8, A0A0L8RL54. The Uniprot entries listed herein are incorporated by reference in their entireties.

Additional homologs of RGT2 are known in the art and such embodiments are within the purview of the present disclosure. For example, the homologs of RGT2 have at least 60%, 65%, 70%, 75%, 80%, 85%, 90%, 95%, or 99% sequence identity to SEQ ID NO: 3.

An example of GPR1 is provided by the sequence of SEQ ID NO: 4, which is GPR1 from *S. cerevisiae*. Homologs of GPR1 from microorganisms other than *S. cerevisiae*, particularly, from yeasts, can be used in the microorganisms and methods of the present disclosure. Non-limiting examples of the homologs of GPR1 are represented by Uniprot entries: A0A1S3ALF0, A0A0Q3MD25, A0A146RBQ8, A0A0P5SHA9, A2ARI4, Q9BXB1, Q9Z2H4, F1MLX5, U3DQD9, I2CVT9, I0FI44, K7D663, K7ASZ6, A0A1U7Q769, U3ESI5, T1E5B8, A0A0F7ZA01, J3RZW5, A0A094ZHC9, W6UL90, A0A0P6J7Q8, L5KYC3, B7P6N0, B0BLW3, A2AHQ2, A0A151N8W7, A0A146RCW3, A0A0X3NYB9, A0A0P5Y3G9, W5UAB2, A0A0P5IC44, A0A090XF51, A0A146NRV7, A0A0X3Q0RO, A0A0P6IRD7, L9JFB7, A0A146YGG2, A0A146WG88, Q12361, B3LGT6, A0A0N8A6F9, P0DM44, W6JM29, A0A1A8LC80, A0A0N8A4D4, Q7Z7M1, A0A1S3G1Q8, A0A1U7QGH1, A6ZXT8, A0A1U8C0F6, D3ZJU9, A0A1S3KGL3, G5B385, L9KNY9, A0A1S3AQM3, A0A087UXX9, A0A0L8VW24, A0A0P6AR08, Q9HBX8, Q3UVD5, A0A1U7UEF2, A0A146XMF9, A0A146QTV1, A0A1S31D45, L5KTU9, A0A1A8ELT4, A0A0N7ZMX8, A0A0P5Q3T8, A0A1A8N9Z4, A0A1A8D807, A0A1A8CVG1, A0A1A8UMB1, A0A1A8JQ07, A0A1A8P7N2, A0A1A8HL38, E7FE13, A0A1S3FZL3, A0A0P7WLQ9, H2KQN3, A0A1S3WJA9, A0A146PKA1, L5LLQ3, F1Q989, A0A0F8AKY3, A0A0P7VR95, A0A1U8C813, A0A034VIM3, A0A0N8BFD4, A0A146XMJ1, A0A0N8BDM1, A0A1A8KTJ1, A0A1A7X706, A0A0R4ITE3, A0A1U7S4H0, A0A1S3AQ94, A0A1U7UCP2, L8HMA8, A0A0Q3P3V6, A0A1A8CDG3, D6W7N2, A0A1E1XMY8, A0A1A8ACL5, A0A1S3WNV2, T0MHY5, A0A1S3G113, V8P2X5, A0A1S3KV51, A0A1S3G018, A0A1S3PUP5, A0A1U8C7X5, S9WP18, A0A1S3AQL8, A0A0N8ENF1, K7CIG0, A0A147BFY7, A0A1S3FZK9, A0A1U7TUH0, A0A1U8BX93, A0A091DKN5, A0A146W919, A0A147B2K7, A0A146XNL4, A0A091DTX9, A0A0Q3UQB0, A0A146WH37, E9QDD1, Q58Y75, A0A096MKI0, A0A1S3S901, Q14BH6, A0A1S3AQ42, A0A0P5SV49, A0A0P5P299, A0A0P5WCR4, K7CHT8, A0A1U7U0Q5, A0A1S3EXD4, A0A146Y6G0, A0A061HXQ0, A0A1S3AQ84, A0A1S2ZNQ3, A0A1U7UEE6, A0A1S3G013, A0A1U7QJG4, S7N7M1, A0A1S3G108, A0A1U8C8H8, and A0A1U8C7X0.

Additional homologs of GPR1 are known in the art and such embodiments are within the purview of the present disclosure. For example, the homologs of GPR1 have at least 60%, 65%, 70%, 75%, 80%, 85%, 90%, 95%, or 99% sequence identity to SEQ ID NO: 4.

In certain embodiments, the microorganisms of the present disclosure comprise genetic modifications that increase the activity of PMA1 in the microorganisms compared to PMA1 activity in the parental microorganisms.

PMA1 protein is an $H^+$ATPase and pumps protons out of the cell, forming a membrane potential used for the uptake of sugars, amino acids, and other nutrients. PMA1 has ten transmembrane domains and three cytoplasmic domains. Both the N and C termini of PMA1 are located in the cytoplasm. Yeast PMA1 has an elongated cytoplasmic tail, which inhibits $H^+$-ATPase activity during glucose starvation. A constitutively active PMA1 lacks the inhibition of $H^+$-ATPase activity during glucose starvation. Therefore, a constitutively active PMA1 is active in the presence of glucose as well as in the absence of glucose.

In particular embodiments of the present disclosure, the microorganisms comprise genetic modifications in pma1 that increase the activity of PMA1 in the microorganisms compared to PMA1 activity in the parental microorganisms. Non-limiting examples of genetic modifications to pma1 that increase the activity of PMA1 in the microorganisms compared to PMA1 activity in the parental microorganisms include one or more of: a) replacement of an endogenous promoter with an exogenous promoter operably linked to the endogenous pma1; b) expression of a pma1 via an extrachromosomal genetic material; c) integration of one or more copies of pma1 into the genome of the microorganism; d) a modification to the endogenous pma1 to produce a modified pma1 that encodes a constitutively active PMA1 or a PMA1 having increased activity compared to the unmodified PMA1, e) introduction into the microorganism an extrachromosomal genetic material comprising a pma1 that encodes a constitutively active PMA1 or a PMA1 having increased activity compared to the corresponding wild-type PMA1; or f) integration into the genome of the microorganism of one or more copies of pma1 that encodes a constitutively active PMA1 or a PMA1 having increased activity compared to the corresponding wild-type PMA1. Any combinations of the mutations a) to f) described in this paragraph are also envisioned.

In some embodiments, an endogenous promoter is replaced with an exogenous promoter that induces the expression of pma1 at a higher level than the endogenous promoter. In certain embodiments, the exogenous promoter is specific for the microorganism in which the exogenous promoter replaces the endogenous promoter. For example, a yeast specific exogenous promoter can be used if the microorganism being modified is a yeast. The exogenous promoter can be a constitutive promoter or inducible promoter.

Non-limiting examples of constitutive yeast specific promoters include: pCyc, pAdh, pSte5, yeast ADH1, cyc100 minimal, cyc70 minimal, cyc43 minimal, cyc28 minimal, cyc16 minimal, pPGK1, pCYC, or pGPD. Additional examples of constitutive promoters from yeast and examples of constitutive promoters from microorganisms other than yeast are known to a skilled artisan and such embodiments are within the purview of the present disclosure.

Non-limiting examples of inducible yeast specific promoters include: Gal1, MFA1, MFA2, Ste3, URA3, FIG1, ENO2, DLD, JEN1, mCYC, and Ste2. Additional examples of inducible promoters from yeast and examples of inducible promoters from microorganisms other than yeast are known to a skilled artisan and such embodiments are within the purview of the present disclosure.

In some embodiments, a genetic modification that increases the activity of PMA1 comprises expressing in a microorganism a PMA1 via an extrachromosomal genetic material comprising a pma1. Extrachromosomal genetic material comprising pma1 and encoding PMA1 typically contains a promoter that controls the expression of PMA1 via pma1. In addition, the extrachromosomal genetic material can also contain a selectable marker gene and an origin of replication.

Depending upon the type of microorganism used, the extrachromosomal genetic material can be a linear or a circular plasmid, a yeast artificial chromosome, or a 2μ circle. Additional examples of extrachromosomal genetic materials suitable for use in the instant disclosure are well known in the art and such embodiments are within the purview of the present disclosure.

In certain embodiments, one or more copies of pma1 are integrated into the genome of the microorganism. In some embodiments, one or more copies of pma1 can have a sequence identical to the endogenous pma1 in the microorganism. In other embodiments, one or more copies of pma1 can have a sequence different from the endogenous pma1 in the microorganism.

In additional embodiments, the endogenous pma1 in a microorganism is inactivated and a pma1 encoding a constitutively active PMA1 is introduced into the microorganism, either as an extrachromosomal genetic material or incorporated into the genome of the microorganism.

Figure 2:
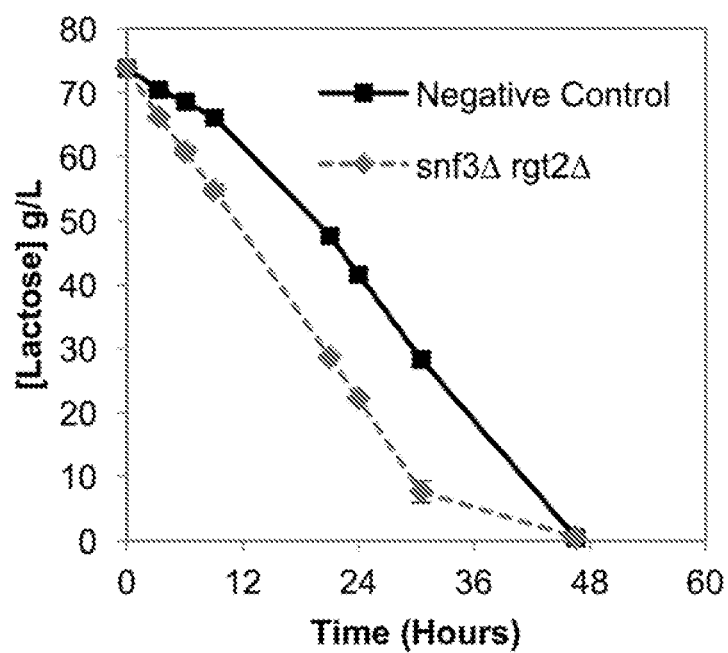
FIG. 2 shows that the disruption of extracellular glucose sensors Snf3 and Rgt2 improves oligosaccharides utilization in the absence of extracellular glucose.

In certain embodiments, the microorganisms comprise a modification to the endogenous pma1 to produce a modified pma1 that encodes a constitutively active PMA1. In some embodiments, the modification to the endogenous pma1 produces a modified pma1 that encodes a constitutively active PMA1 comprising mutations described by Mason et al. (2014), *Eukaryotic Cell* 13: 43-52. The Mason et al. reference, particularly, FIG. 1 and FIG. 2, is herein incorporated by reference in its entirety.

Accordingly, in certain embodiments, modification to the endogenous pma1 produces a modified pma1 that encodes a constitutively active PMA1, which is a PMA1 lacking at least two to about thirty, preferably, at least three to about thirty, amino acids from the C-terminus as compared to the corresponding wild-type PMA1. In certain embodiments, *S. cerevisiae* having an endogenous pma1 encoding PMA1 of SEQ ID NO: 1 is genetically modified to produce a modified pma1 that encodes a truncated PMA1 lacking at least two to about thirty, preferably, at least three to about thirty, amino acids from the C-terminus of SEQ ID NO: 1.

In some embodiments, *S. cerevisiae* having an endogenous pma1 encoding PMA1 of SEQ ID NO: 1 is genetically modified to produce a modified PMA1 having increased activity, wherein the modified PMA1 that has serine at 911 position of SEQ ID NO: 1 mutated to aspartic acid and/or threonine at 912 position of SEQ ID NO: 1 mutated to aspartic acid. In certain embodiments, *S. cerevisiae* having an endogenous pma1 encoding PMA1 of SEQ ID NO: 1 is genetically modified as described in Chomvong et al., BioRxiv preprint, available at world-wide-website: dx.doi.org/10.1101/076364. The Chomvong et al. reference is herein incorporated by reference in its entirety.

In some embodiments, the modifications that increase the activity of PMA1 comprise one or more modifications to one or more of torc1, fpr1, and/or sit4. The mutations in torc1, fpr1, and/or sit4 that increase the activity of PMA1 include the mutations described in Mahmoud et al. (2017), *FEBS Lett.*, doi: 10.1002/1873-3468.12673. The Mahmoud et al. reference is herein incorporated by reference in its entirety.

In some embodiments, an extrachromosomal genetic material comprising one or more copies of a pma1 that encodes a constitutively active PMA1 is introduced into a microorganism. The extrachromosomal genetic material comprising a pma1 that encodes a constitutively active PMA1 can be under the control of a constitutive or inducible promoter. The constitutive or inducible promoters described earlier can be used in such embodiments.

In further embodiments, one or more copies of a pma1 that encodes a constitutively active PMA1 is integrated into the genome of the microorganism. The pma1 that encodes a constitutively active PMA1 and incorporated into the genome of the microorganisms can be under the control of a constitutive or an inducible promoter. The constitutive or inducible promoters described earlier can be used in such embodiments.

In certain embodiments, the microorganisms of the present disclosure comprise genetic modifications that decrease or eliminate the activities of SNF3, RGT2, and/or GPR1 in the microorganisms compared to the activities of the corresponding proteins in the parental microorganisms.

SNF3 protein is a plasma membrane low glucose sensor that regulates glucose transport. It is a high affinity sensor that contains 12 predicted transmembrane segments and a long C-terminal tail required for induction of hexose transporters. SNF3 also senses fructose and mannose.

RGT2 is a plasma membrane high glucose sensor that regulates glucose transport. It is a low affinity sensor that contains 12 predicted transmembrane segments and a long C-terminal tail required for hexose transporter induction. Phosphorylation of the tail by Yck1p/Yck2p facilitates binding to the HXT co-repressors, Mth1p and Std1p.

GPR1 is a G protein-coupled receptor that interacts with the Gpa2p and Plc1p proteins to integrate carbon and nitrogen nutritional signaling through cAMP and PKA pathways.

In certain embodiments, the genetic modifications that decrease or eliminate the activities of SNF3, RGT2, and/or GPR1 in the microorganisms compared to the activities of the corresponding proteins in the parental microorganisms comprise one or more genetic modification to nucleotide binding alpha subunit of the heterotrimeric G protein (GPA2) that inactivate or eliminate the activity of GPA2. Examples of mutations in GPA2 that can reduce or eliminate the activities of SNF3, RGT2, and/or GPR1 are provided in Nazarko et al. (2008), *Cell Biol Int.;* 32 (5):502-4. The Nazarko et al. reference is herein incorporated by reference in its entirety.

In some embodiments, the genetic modifications that decrease or eliminate the activities of SNF3, RGT2, and/or GPR1 in the microorganisms compared to the activities of the corresponding proteins in the parental microorganisms comprise one or more genetic modification to nucleotide binding alpha subunit of the heterotrimeric G protein (GPA2) that inactivate or eliminate the activity of GPA2 comprise one or more mutations in genes encoding HTR1, MTH1, and/or RGT1 proteins. Examples of mutations in HTR1, MTH1, and/or RGT1 proteins that can reduce or eliminate the activities of SNF3, RGT2, and/or GPR1 are provided in Schulte et al. (2000), *J Bacteriol.;* 182 (2):540-2. The Schulte et al. reference is herein incorporated by reference in its entirety.

Additional mutations that decrease or eliminate the activities of SNF3, RGT2, and/or GPR1 in the microorganisms compared to the activities of the corresponding proteins in the parental microorganisms are known in the art and such embodiments are within the purview of the present disclosure.

In particular embodiments, the microorganisms of the present disclosure comprise genetic modifications in snf3, rgt2, and/or gpr1 that decrease or eliminate the activities of SNF3, RGT2, and/or GPR1 in the microorganisms compared to the activities of corresponding proteins in the parental microorganisms.

In some embodiments, the genetic modifications that decrease or eliminate the activities of SNF3, RGT2, and/or GPR1 comprise one or more of: a) an inactivation of snf3, rgt2, and/or gpr1, wherein the inactivated snf3, rgt2, and/or gpr1 does not encode SNF3, RGT2, and/or GPR1; b) a mutation in snf3, rgt2, and/or gpr1, wherein the mutated snf3, rgt2, and/or gpr1 encodes for the SNF3, RGT2, and/or GPR1 having no activity or reduced activity compared to the activity of the corresponding protein in the parental microorganism; c) a mutation in the promoter for snf3, rgt2, and/or gpr1, wherein the mutated promoter causes reduced expression of SNF3, RGT2, and/or GPR1 compared to the expression of the corresponding protein in the parental microorganism; d) a replacement of an endogenous promoter from snf3, rgt2, and/or gpr1 with an exogenous promoter operably linked to the coding region of the endogenous snf3, rgt2, and/or gpr1, wherein the exogenous promoter causes no expression or reduced expression of SNF3, RGT2, and/or GPR1 compared to the expression of the corresponding protein in the parental microorganism. Any combinations of the mutations a) to d) described in this paragraph are also envisioned.

The inactivation of snf3, rgt2, and/or gpr1 can be achieved by one or more of: a) a complete or partial deletion of the coding region; b) introduction of a frame shift mutation within the coding region; c) insertion of one or more nucleotides in a manner that disrupts the activity of SNF3, RGT2, and/or GPR1; d) introduction of a stop codon in the coding region; or any combination of a) to d) described in this paragraph. In some embodiments, endogenous snf3, rgt2, and/or gpr1 can be replaced with a mutated snf3, rgt2, and/or gpr1 that does not encode SNF3, RGT2, and/or GPR1.

In specific embodiments, the present disclosure provides a microorganism, preferably, a yeast, more preferably, a *Saccharomyces* spp., and even more preferably, *S. cerevisiae*, the microorganism comprising the genetic modifications or the combinations of genetic modifications listed below:

1) a genetic modification producing a PMA1 having increased activity compared to the corresponding unmodified PMA1 or a constitutively active PMA1 and a genetic modification causing inactivation of snf3, 2) a genetic modification producing a PMA1 having increased activity compared to the corresponding unmodified PMA1 or a constitutively active PMA1 and a genetic modification causing inactivation of rgt2, 3) a genetic modification producing a PMA1 having increased activity compared to the corresponding unmodified PMA1 or a constitutively active PMA1 and a genetic modification causing inactivation of gpr1, 4) a genetic modification producing a PMA1 having increased activity compared to the corresponding unmodified PMA1 or a constitutively active PMA1, a genetic modification causing inactivation of snf3, and a genetic modification causing inactivation of rgt2, 5) a genetic modification producing a PMA1 having increased activity compared to the corresponding unmodified PMA1 or a constitutively active PMA1, a genetic modification causing inactivation of snf3, and a genetic modification causing inactivation of gpr1, 6) a genetic modification producing a PMA1 having increased activity compared to the corresponding unmodified PMA1 or a constitutively active PMA1, a genetic modification causing inactivation of rgt2, and a genetic modification causing inactivation of gpr1, 7) a genetic modification causing inactivation of snf3 and a genetic modification causing inactivation of rgt2, 8) a genetic modification causing inactivation of snf3 and a genetic modification causing inactivation of gpr1, 9) a genetic modification causing inactivation of rgt2 and a genetic modification causing inactivation of gpr1, 10) a genetic modification causing inactivation of snf3, a genetic modification causing inactivation of rgt2, and a genetic modification causing inactivation of gpr1, 11) a genetic modification producing a PMA1 having increased activity compared to the corresponding unmodified PMA1 or a constitutively active PMA1, a genetic modification causing inactivation of snf3, a genetic modification causing inactivation of rgt2, and a genetic modification causing inactivation of gpr1, 12) a genetic modification producing a PMA1 having increased activity compared to the corresponding unmodified PMA1 or a constitutively active PMA1 having a truncation of at least two to about thirty, particularly, at least three to about thirty amino acids, at the C-terminus of PMA1 having a sequence of SEQ ID NO: 1 or a homolog thereof having at least 90%, preferably, at least 95%, sequence identity to SEQ ID NO: 1, a genetic modification causing inactivation of snf3, and a genetic modification causing inactivation of rgt2, 13) a genetic modification producing a PMA1 having increased activity compared to the corresponding unmodified PMA1 or a constitutively active PMA1 having a truncation of at least two to about thirty, particularly, at least three to about thirty amino acids, at the C-terminus of PMA1 having a sequence of SEQ ID NO: 1 or a homolog thereof having at least 90%, preferably, at least 95%, sequence identity to SEQ ID NO: 1, a genetic modification causing inactivation of snf3, and a genetic modification causing inactivation of gpr1, 14) a genetic modification producing a PMA1 having increased activity compared to the corresponding unmodified PMA1 or a constitutively active PMA1 having a truncation of at least two to about thirty, particularly, at least three to about thirty amino acids, at the C-terminus of PMA1 having a sequence of SEQ ID NO: 1 or a homolog thereof having at least 90%, preferably, at least 95%, sequence identity to SEQ ID NO: 1, a genetic modification causing inactivation of rgt2, and a genetic modification causing inactivation of gpr1, 15) a genetic modification producing a PMA1 having increased activity compared to the corresponding unmodified PMA1 or a constitutively active PMA1 having a truncation of at least two to about thirty, particularly, at least three to about thirty amino acids, at the C-terminus of.
PMA1 having a sequence of SEQ ID NO: 1 or a homolog thereof having at least 90%, preferably, at least 95%, sequence identity to SEQ ID NO: 1, a genetic modification causing inactivation of snf3, a genetic modification causing inactivation of rgt2, and a genetic modification causing inactivation of gpr1, 16) a genetic modification producing a PMA1 having increased activity compared to the corresponding unmodified PMA1 or a constitutively active PMA1 having a truncation of two or three amino acids at the C-terminus of PMA1 having a sequence of SEQ ID NO: 1 or a homolog thereof having at least 90%, preferably, at least 95%, sequence identity to SEQ ID NO: 1, a genetic modification causing inactivation of snf3, and a genetic modification causing inactivation of rgt2, 17) a genetic modification producing a PMA1 having increased activity compared to the corresponding unmodified PMA1 or a constitutively active PMA1 having a truncation of at least two or three amino acids at the C-terminus of PMA1 having a sequence of SEQ ID NO: 1 or a homolog thereof having at least 90%, preferably, at least 95%, sequence identity to SEQ ID NO: 1, a genetic modification causing inactivation of snf3, and a genetic modification causing inactivation of gpr1, 18) a genetic modification producing a PMA1 having increased activity compared to the corresponding unmodified PMA1 or a constitutively active PMA1 having a truncation of at least two or three amino acids at the C-terminus of PMA1 having a sequence of SEQ ID NO: 1 or a homolog thereof having at least 90%, preferably, at least 95%, sequence identity to SEQ ID NO: 1, a genetic modification causing inactivation of rgt2, and a genetic modification causing inactivation of gpr1, 19) a genetic modification producing a PMA1 having increased activity compared to the corresponding unmodified PMA1 or a constitutively active PMA1 having a truncation of at least two or three amino acids at the C-terminus of PMA1 having a sequence of SEQ ID NO: 1 or a homolog thereof having at least 90%, preferably, at least 95%, sequence identity to SEQ ID NO: 1, a genetic modification causing inactivation of snf3, a genetic modification causing inactivation of rgt2, and a genetic modification causing inactivation of gpr1, 20) a genetic modification producing a PMA1 having increased activity compared to the corresponding unmodified PMA1 or a constitutively active PMA1 having a truncation of at least two or three amino acids at the C-terminus of PMA1 having a sequence of SEQ ID NO: 1 or a homolog thereof having at least 90%, preferably, at least 95%, sequence identity to SEQ ID NO: 1, a genetic modification causing inactivation of snf3, 21) a genetic modification producing a PMA1 having increased activity compared to the corresponding unmodified PMA1 or a constitutively active PMA1 having a truncation of at least two or three amino acids at the C-terminus of PMA1 having a sequence of SEQ ID NO: 1 or a homolog thereof having at least 90%, preferably, at least 95%, sequence identity to SEQ ID NO: 1, a genetic modification causing inactivation of rgt2, 22) a genetic modification producing a PMA1 having increased activity compared to the corresponding unmodified PMA1 or a constitutively active PMA1 having a truncation of at least two to about thirty, particularly, at least three to about thirty amino acids, at the C-terminus of PMA1 having a sequence of SEQ ID NO: 1 or a homolog thereof having at least 90%, preferably, at least 95%, sequence identity to SEQ ID NO: 1, and a genetic modification causing inactivation of gpr1.

In some embodiments, the genetically engineered microorganisms further comprise an exogenous nucleotide sequence encoding a chaperonin. In preferred embodiments, the chaperonin is GroESL.

In some embodiments, the genetically modified microorganisms disclosed herein may comprise an alteration of PMA1 activity. In preferred embodiments, the alternation results in a PMA1 having increased activity compared to the corresponding unmodified PMA1 or constitutive activity of PMA1 and improved oligosaccharides utilization, with or without the presence of extracellular glucose. For example, the last three amino acids before the stop codon of the pma1 may be eliminated (pma1-916Δ) for improved oligosaccharide consumption (e.g., see FIG. 1).

In further embodiments, the genetically engineered microorganisms disclosed herein may comprise an alteration of extracellular glucose sensors activity. In preferred embodiments, the alternation results in elimination or reduction of extracellular glucose sensing for improved oligosaccharides utilization, with or without the presence of extracellular glucose. For example, the coding sequences of snf3 and rgt2 may be eliminated (snf3Δrgt2Δ) for improved oligosaccharides consumption (e.g., see FIG. 2).

In particular embodiments, the genetically engineered microorganisms disclosed herein may comprise an alteration of PMA1 activity and elimination or reduction of extracellular glucose sensors activity. For example, the last three amino acids before the stop codon of pma1 may be eliminated and the coding sequences of snf3 and rgt2 (PMA1-916Δsnf3Δrgt2Δ) are inactivated from the microorganisms for improved oligosaccharides consumption (e.g., see FIG. 3).

Figure 4:
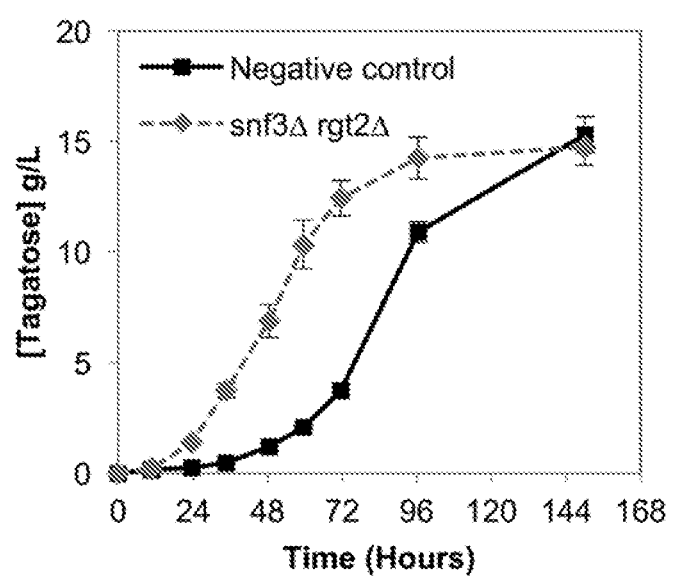
FIG. 4 shows the increase of tagatose, as an example of desirable product, productivity in a strain with Snf3 and Rgt2 disruption.

In specific embodiments, the genetically engineered microorganisms disclosed herein may comprise an alteration of PMA1 activity and/or extracellular glucose sensors activity for improved production of desired compound (e.g., tagatose, 2'-fucosyllactose, psicose, human milk oligosaccharides). For example, the microorganisms with snf3Δrgt2Δ, the productivity of tagatose, as calculated from the areas under the curve, is improved by 52% (e.g., see FIG. 4).

Microorganisms used to produce the genetically modified microorganisms described herein may be selected from *Saccharomyces* spp., such as *S. cerevisiae, S. pastorianus, S. beticus, S. fermentati, S. paradoxus, S. uvarum* and *S. bayanus; Schizosaccharomyces* spp. such as *S. pombe, S. japonicus, S. octosporus* and *S. cryophilus; Torulaspora* spp. such as *T. delbrueckii; Kluyveromyces* spp. such as *K. marxianus; Pichia* spp. such as *P. stipitis, P. pastoris* or *P. angusta, Zygosaccharomyces* spp. such as *Z. bailii; Brettanomyces* spp. such as *B. inter medius, B. bruxellensis, B. anomalus, B. custersianus, B. naardenensis, B. minus; Dekkera* spp., such as *D. bruxellensis* and *D. anomala; Metschmkowia* spp.; *Issatchenkia* spp. such as *I. orientalis, Kloeckera* spp. such as *K.apiculata; Aureobasidium* spp. such as *A. pullulans*.

In some embodiments, in addition to the genetic modifications producing the changes in PMA1, SNF3, RGT2, and/or GPR1, the microorganisms described herein further comprise: modulated GDP-L-fucose biosynthetic pathway; introduction of an exogenous polynucleotide encoding α-1,2 fucosyltransferase; and/or a weak β-galactosidase activity.

The GDP-L-fucose synthesis pathway can be modulated by at least one of: increased GDP-o-mannose biosynthesis, regeneration of NADPH, and manipulation of the guanosine nucleotides biosynthetic pathway. The exogenous α-1,2 fucosyltransferase can be from *Helicobacter pylori, Caenorhabditis elegans, Rattus norvegicus, Mus musculus, Escherichia coli, Bacteroides fragilis*, or a *Homo sapiens*.

In some embodiments, the microorganisms comprise a two-step oxidoreductive pathway. The two-step oxidoreductive pathway can comprise an aldose reductase and a galactitol-2-dehydrogenase.

In addition to the genetic modifications producing the changes in PMA1, SNF3, RGT2, and GPR1, the microorganisms described herein further comprise the genetic modifications described in U.S. Pat. Nos. 8,431,360, 8,765,410, 9,012,177 and United States Patent Application Publications 20170152538, all of which are herein incorporated by reference in their entirety.

The microorganisms of the present disclosure are capable of utilizing an oligosaccharide, for example, sucrose, lactose, maltose, isomaltose, isomaltulose, trehalose, trehaulose, cellobiose, cellotriose, cellotetraose, cellopentaose, or cellohexaose. In particular embodiments, the microorganisms described herein have higher capacity, compared to the parental microorganisms, of utilizing an oligosaccharide. In specific embodiments, the utilization of an oligosaccharide occurs in the cytosol of the microorganisms.

In some embodiments, the microorganisms described herein are capable of converting lactose into tagatose. In particular embodiments, the microorganisms described herein have higher capacity, compared to the parental microorganisms, of converting lactose into tagatose. In specific embodiments, the conversion of lactose into tagatose occurs in the cytosol of the microorganisms.

Figure 9:
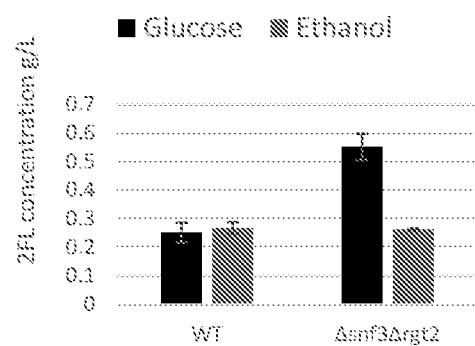
FIG. 9 shows the increase of 2FL, as an example of desirable product, productivity in a strain with Snf3 and Rgt2 disruption.

In some embodiments, the microorganisms described herein are capable of converting lactose into 2'-FL. In particular embodiments, the microorganisms described herein have higher capacity, compared to the parental microorganisms, of converting lactose into 2'-FL (e.g. see FIG. 9). In specific embodiments, the conversion of lactose into 2'-FL occurs in the cytosol of the microorganisms.

In some embodiments, the microorganisms are capable of converting sucrose into psicose. In particular embodiments, the microorganisms described herein have higher capacity, compared to the parental microorganisms, of converting sucrose into psicose. In specific embodiments, the conversion of sucrose into psicose occurs in the cytosol of the microorganisms.

Accordingly, further embodiments of the present disclosure provide methods of producing products of interest by culturing the microorganisms described herein in appropriate media containing an appropriate oligosaccharide under appropriate conditions for appropriate period of time and recovering the product of interest from the culture media.

In certain embodiments, the present disclosure provides methods of producing tagatose by culturing the microorganisms described herein in culture media containing lactose under appropriate conditions for appropriate period of time and recovering tagatose from the culture media.

In certain embodiments, the present disclosure provides methods of producing 2'-FL by culturing the microorganisms described herein in culture media containing lactose under appropriate conditions for appropriate period of time and recovering 2'-FL from the culture media.

In certain embodiments, the present disclosure provides methods of producing psicose by culturing the microorganisms described herein in culture media containing sucrose under appropriate conditions for appropriate period of time and recovering psicose from the culture media.

In preferred embodiments, the microorganisms belong to *Saccharomyces* spp. In even more preferred embodiments, the microorganisms are *S. cerevisiae*.

In certain embodiments, the media contains about 10 g/L yeast extract, 20 g/L peptone, and about 40 g/L oligosaccharide, particularly, lactose or sucrose. In particular embodiments, the microorganisms, particularly, yeast, are grown at 30° C.

Additional culture media, conditions appropriate for culturing the microorganisms, and the methods of recovering the products of interest from the culture media are well known in the art and such embodiments are within the purview of the present disclosure.

EXAMPLES

Strains and Media

*S. cerevisiae* was grown and maintained on YPD medium (10 g/L yeast extract, 20 g/L peptone, 20 g/L glucose) at 30° C. All genes were expressed chromosomally. The oligosaccharide utilizing strain contains cellobiose transporter (CDT-1) and beta-glucosidase (GH1-1). The tagatose production strain contains CDT-1, GH1-1 and xylose reductase (XR), galactitol 2-dehydrogenase (GDH)). pma1-916Δ mutation had c-terminal truncation as described by Mason et al. The coding regions of snf3 and rgt2 were eliminated in snf3Δrgt2Δ strain. The experiments were conducted in YPL medium (10 g/L yeast extract, 20 g/L peptone, 40 g/L lactose) at 30° C.

Fermentation and Metabolite Analysis

Triplicates of single colonies were inoculated in 20 mL of YPD at 30° C. overnight. The cells were centrifuged and washed twice with sterile water. The final fermentation volume was 5 mL in YPL medium. The initial optical density at 600 nm was 20. The cells were incubated at 30° C. and 250 rpm. Lactose concentration was determined by high performance liquid chromatography on a Prominence HPLC (Shimazu, Kyoto, Japan) equipped with Rezex RFQ-FastAcid H 10×7.8 mm column. The column was eluted with 0.01 N of sulfuric acid at a flow rate of 1 mL/min, 55° C. Tagatose concentration as determined using an ICS-3000 Ion Chromatography System (Dionex, Sunnyvale, Calif., USA) equipped with CarboPac PA20 column. The column was eluted with KOH gradient at a flow rate of 0.4 mL/min, 30° C.

The introduction of constitutively active Pma1 improves oligosaccharides utilization in the absence of extracellular glucose (e.g., FIG. 1). The last three amino acids before the stop codon of the pma1 were eliminated (pma1-916Δ) for improved oligosaccharide consumption. The elimination or reduction of snf3 and rgt2 improved oligosaccharides utilization, with or without the presence of extracellular glucose (e.g., see FIG. 2). The coding sequences of snf3 and rgt2 were eliminated (snf3Δrgt2Δ) for improved oligosaccharides consumption. The genetic modification was performed for improved production of desired compound (e.g., tagatose, 2'-fucosyllactose, psicose, human milk oligosaccharides). For example, the microorganisms with snf3Δrgt2Δ, the productivity of tagatose, as calculated from the areas under the curve, is improved by 52% (e.g., see FIG. 4). The microorganisms with snf3Δrgt2Δ are capable of converting lactose into 2'-FL. The microorganisms with snf3Δrgt2Δ have higher capacity, compared to the parental microorganisms, of converting lactose into 2'-FL (e.g. see FIG. 9)

Figure 3:
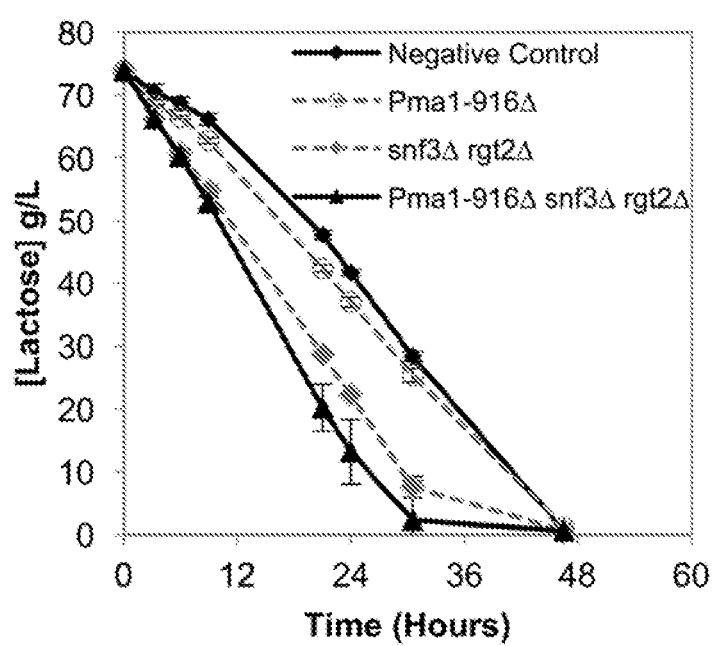
FIG. 3 shows that the combination of constitutively active Pma1 and disruption of Snf3 Rgt2 extracellular glucose sensors synergistically improves oligosaccharides utilization in the absence of extracellular glucose.

The combination of introduction of constitutively active Pma1 and elimination or reduction of snf3 and rgt2 synergistically improved oligosaccharides utilization in the absence of extracellular glucose (e.g., see FIG. 3). The last three amino acids before the stop codon of pma1 were eliminated and the coding sequences of snf3 and rgt2 (PMA1-916Δsnf3Δrgt2Δ) were inactivated from the microorganisms for improved oligosaccharides consumption.

INCORPORATION BY REFERENCE

Each of the patents, published patent applications, and non-patent references cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of producing a lactose-containing human milk oligosaccharide (HMO), comprising providing a culture medium with lactose;

culturing a microorganism on the medium, wherein the microorganism produces a lactose-containing HMO; and harvesting the lactose-containing HMO, wherein the microorganism is a filamentous fungus or a yeast, and wherein the microorganism comprises a genetic modification that decreases the activity of sucrose non-fermenting protein 3 (SNF3A in the microorganism compared to SNF3 activity in the parental microorganism, a genetic modification that decreases the activity of restores glucose transport protein 2 (RGT2A in the microorganism compared to RGT2 activity in the parental microorganism, and an exogenous polynucleotide encoding an α-1,2-fucosyltransferase.

2. The method of claim 1, wherein the microorganism is selected from the group consisting of *Saccharomyces cerevisiae, S. pastorianus, S. beticus, S. fermentati, S. paradoxus, S. uvarum, S. bayanus, Schizosaccharomyces pombe, S. japonicus, S. octosporus, S. cryophilus, Torulaspora delbrueckii, Kluyveromyces marxianus, Pichia stipitis, P. pastoris, P. angusta, Zygosaccharomyces bailii, Brettanomyces inter medius, B. bruxellensis, B. anomalus, B. custersianus, B. naardenensis, B. nanus, Dekkera bruxellensis, D. anomala, Metschmkowia* spp., *Issatchenkia orientalis, Kloeckera apiculate*, and *Aureobasidium pullulans*.

3. The method of claim 1, wherein the lactose-containing HMO is 2'fucosyllactose (2'-FL) or lacto-N-tetraose (LNT).

4. The method of claim 1, wherein the lactose-containing HMO is secreted from the microorganism and the lactose-containing HMO is harvested from the culture medium.

5. The method of claim 1, wherein the microorganism further comprises a GDP-L-fucose biosynthetic pathway.

6. The method of claim 5, wherein the α-1,2 fucosyltransferase is heterologous to the microorganism and wherein the lactose-containing HMO is (2'-FL).

7. The method of claim 1, wherein the genetic modification that decreases the activity of SNF3 and/or RGT2 comprises one or more of: a) a complete or partial deletion of the coding region of SNF3 and/or RGT2; b) introduction of a frame shift mutation within the coding region of SNF3 and/or RGT2; c) insertion of one or more nucleotides in a manner that disrupts the activity of SNF3 and/or RGT2; d) introduction of a stop codon in the coding region of SNF3 and/or RGT2; or e) any combination of a) to d).

8. The method of claim 1, wherein the genetic modification that decreases the activity of RGT2 comprises a mutated rgt2 that does not express an active RGT2 protein.

9. The method of claim 1, wherein the microorganism further comprises a genetic modification that increases the activity of plasma membrane ATPase protein 1 (PMA1) in the microorganism compared to PMA1 activity in the parental microorganism, wherein the genetic modification comprises a genetic modification to increase expression of PMA1, a genetic modification to express a C-terminally truncated constitutively active PMA1, or a genetic modification to replace serine with aspartate at position 911 of SEQ ID NO: 1 and/or to replace threonine with aspartate at position 912 of SEQ ID NO: 1.

10. The method of claim 1, wherein the microorganism further comprises a genetic modification that decreases the activity of G protein-coupled receptor 1 (GPR1) in the microorganism compared to GPR1 activity in the parental microorganism.

11. The method of claim 9, wherein the microorganism further comprises a genetic modification that decreases the activity of GPR1 in the microorganism compared to GPR1 activity in the parental microorganism.

* * * * *

SEQUENCE LISTING

<160> NUMBER OF SEQ ID NOS: 4

<210> SEQ ID NO 1

```
<211> LENGTH: 918
<212> TYPE: PRT
<213> ORGANISM: Saccharomyces cerevisiae

<400> SEQUENCE: 1

Met Thr Asp Thr Ser Ser Ser Ser Ser Ser Ala Ser Ser Val
1               5                   10                  15

Ser Ala His Gln Pro Thr Gln Glu Lys Pro Ala Lys Thr Tyr Asp Asp
                20                  25                  30

Ala Ala Ser Glu Ser Ser Asp Asp Asp Ile Asp Ala Leu Ile Glu
            35                  40                  45

Glu Leu Gln Ser Asn His Gly Val Asp Gly Asp Ser Asp Asn Asp
50                  55                      60

Gly Pro Val Ala Ala Gly Glu Ala Arg Pro Val Pro Glu Glu Tyr Leu
65                  70                  75                  80

Gln Thr Asp Pro Ser Tyr Gly Leu Thr Ser Asp Glu Val Leu Lys Arg
                85                  90                  95

Arg Lys Lys Tyr Gly Leu Asn Gln Met Ala Asp Glu Lys Glu Ser Leu
                100                 105                 110

Val Val Lys Phe Val Met Phe Phe Val Gly Pro Ile Gln Phe Val Met
            115                 120                 125

Glu Ala Ala Ala Ile Leu Ala Ala Gly Leu Ser Asp Trp Val Asp Phe
130                 135                 140

Gly Val Ile Cys Gly Leu Leu Met Leu Asn Ala Gly Val Gly Phe Val
145                 150                 155                 160

Gln Glu Phe Gln Ala Gly Ser Ile Val Asp Glu Leu Lys Lys Thr Leu
                165                 170                 175

Ala Asn Thr Ala Val Val Ile Arg Asp Gly Gln Leu Val Glu Ile Pro
            180                 185                 190

Ala Asn Glu Val Val Pro Gly Asp Ile Leu Gln Leu Glu Asp Gly Thr
        195                 200                 205

Val Ile Pro Thr Asp Gly Arg Ile Val Thr Glu Asp Cys Phe Leu Gln
210                 215                 220

Ile Asp Gln Ser Ala Ile Thr Gly Glu Ser Leu Ala Val Asp Lys His
225                 230                 235                 240

Tyr Gly Asp Gln Thr Phe Ser Ser Ser Thr Val Lys Arg Gly Glu Gly
                245                 250                 255

Phe Met Val Val Thr Ala Thr Gly Asp Asn Thr Phe Val Gly Arg Ala
            260                 265                 270

Ala Ala Leu Val Asn Lys Ala Ala Gly Gly Gln Gly His Phe Thr Glu
        275                 280                 285

Val Leu Asn Gly Ile Gly Ile Ile Leu Leu Val Leu Val Ile Ala Thr
290                 295                 300

Leu Leu Leu Val Trp Thr Ala Cys Phe Tyr Arg Thr Asn Gly Ile Val
305                 310                 315                 320

Arg Ile Leu Arg Tyr Thr Leu Gly Ile Thr Ile Ile Gly Val Pro Val
                325                 330                 335

Gly Leu Pro Ala Val Val Thr Thr Thr Met Ala Val Gly Ala Ala Tyr
            340                 345                 350

Leu Ala Lys Lys Gln Ala Ile Val Gln Lys Leu Ser Ala Ile Glu Ser
        355                 360                 365

Leu Ala Gly Val Glu Ile Leu Cys Ser Asp Lys Thr Gly Thr Leu Thr
370                 375                 380

Lys Asn Lys Leu Ser Leu His Glu Pro Tyr Thr Val Glu Gly Val Ser
```

-continued

```
            385                 390                 395                 400
        Pro Asp Asp Leu Met Leu Thr Ala Cys Leu Ala Ala Ser Arg Lys Lys
                            405                 410                 415

Lys Gly Leu Asp Ala Ile Asp Lys Ala Phe Leu Lys Ser Leu Lys Gln
                            420                 425                 430

Tyr Pro Lys Ala Lys Asp Ala Leu Thr Lys Tyr Lys Val Leu Glu Phe
                            435                 440                 445

His Pro Phe Asp Pro Val Ser Lys Lys Val Thr Ala Val Val Glu Ser
                            450                 455                 460

Pro Glu Gly Glu Arg Ile Val Cys Val Lys Gly Ala Pro Leu Phe Val
        465                 470                 475                 480

Leu Lys Thr Val Glu Glu Asp His Pro Ile Pro Glu Asp Val His Glu
                            485                 490                 495

Asn Tyr Glu Asn Lys Val Ala Glu Leu Ala Ser Arg Gly Phe Arg Ala
                            500                 505                 510

Leu Gly Val Ala Arg Lys Arg Gly Glu Gly His Trp Glu Ile Leu Gly
                            515                 520                 525

Val Met Pro Cys Met Asp Pro Pro Arg Asp Asp Thr Ala Gln Thr Val
                            530                 535                 540

Ser Glu Ala Arg His Leu Gly Leu Arg Val Lys Met Leu Thr Gly Asp
        545                 550                 555                 560

Ala Val Gly Ile Ala Lys Glu Thr Cys Arg Gln Leu Gly Leu Gly Thr
                            565                 570                 575

Asn Ile Tyr Asn Ala Glu Arg Leu Gly Leu Gly Gly Gly Asp Met
                            580                 585                 590

Pro Gly Ser Glu Leu Ala Asp Phe Val Glu Asn Ala Asp Gly Phe Ala
                            595                 600                 605

Glu Val Phe Pro Gln His Lys Tyr Arg Val Val Glu Ile Leu Gln Asn
                            610                 615                 620

Arg Gly Tyr Leu Val Ala Met Thr Gly Asp Gly Val Asn Asp Ala Pro
        625                 630                 635                 640

Ser Leu Lys Lys Ala Asp Thr Gly Ile Ala Val Glu Gly Ala Thr Asp
                            645                 650                 655

Ala Ala Arg Ser Ala Ala Asp Ile Val Phe Leu Ala Pro Gly Leu Ser
                            660                 665                 670

Ala Ile Ile Asp Ala Leu Lys Thr Ser Arg Gln Ile Phe His Arg Met
                            675                 680                 685

Tyr Ser Tyr Val Val Tyr Arg Ile Ala Leu Ser Leu His Leu Glu Ile
                            690                 695                 700

Phe Leu Gly Leu Trp Ile Ala Ile Leu Asp Asn Ser Leu Asp Ile Asp
        705                 710                 715                 720

Leu Ile Val Phe Ile Ala Ile Phe Ala Asp Val Ala Thr Leu Ala Ile
                            725                 730                 735

Ala Tyr Asp Asn Ala Pro Tyr Ser Pro Lys Pro Val Lys Trp Asn Leu
                            740                 745                 750

Pro Arg Leu Trp Gly Met Ser Ile Ile Leu Gly Ile Val Leu Ala Ile
                            755                 760                 765

Gly Ser Trp Ile Thr Leu Thr Thr Met Phe Leu Pro Lys Gly Gly Ile
                            770                 775                 780

Ile Gln Asn Phe Gly Ala Met Asn Gly Ile Met Phe Leu Gln Ile Ser
        785                 790                 795                 800

Leu Thr Glu Asn Trp Leu Ile Phe Ile Thr Arg Ala Ala Gly Pro Phe
                            805                 810                 815
```

-continued

```
Trp Ser Ser Ile Pro Ser Trp Gln Leu Ala Gly Ala Val Phe Ala Val
            820                 825                 830

Asp Ile Ile Ala Thr Met Phe Thr Leu Phe Gly Trp Trp Ser Glu Asn
            835                 840                 845

Trp Thr Asp Ile Val Thr Val Val Arg Val Trp Ile Trp Ser Ile Gly
850                 855                 860

Ile Phe Cys Val Leu Gly Gly Phe Tyr Tyr Glu Met Ser Thr Ser Glu
865                 870                 875                 880

Ala Phe Asp Arg Leu Met Asn Gly Lys Pro Met Lys Glu Lys Lys Ser
            885                 890                 895

Thr Arg Ser Val Glu Asp Phe Met Ala Ala Met Gln Arg Val Ser Thr
            900                 905                 910

Gln His Glu Lys Glu Thr
            915

<210> SEQ ID NO 2
<211> LENGTH: 884
<212> TYPE: PRT
<213> ORGANISM: Saccharomyces cerevisiae

<400> SEQUENCE: 2

Met Asp Pro Asn Ser Asn Ser Ser Glu Thr Leu Arg Gln Glu Lys
1               5                   10                  15

Gln Gly Phe Leu Asp Lys Ala Leu Gln Arg Val Lys Gly Ile Ala Leu
            20                  25                  30

Arg Arg Asn Asn Ser Asn Lys Asp His Thr Thr Asp Asp Thr Thr Gly
        35                  40                  45

Ser Ile Arg Thr Pro Thr Ser Leu Gln Arg Gln Asn Ser Asp Arg Gln
    50                  55                  60

Ser Asn Met Thr Ser Val Phe Thr Asp Asp Ile Ser Thr Ile Asp Asp
65                  70                  75                  80

Asn Ser Ile Leu Phe Ser Glu Pro Pro Gln Lys Gln Ser Met Met Met
                85                  90                  95

Ser Ile Cys Val Gly Val Phe Ala Val Gly Gly Phe Leu Phe Gly
            100                 105                 110

Tyr Asp Thr Gly Leu Ile Asn Ser Ile Thr Ser Met Asn Tyr Val Lys
        115                 120                 125

Ser His Val Ala Pro Asn His Asp Ser Phe Thr Ala Gln Gln Met Ser
    130                 135                 140

Ile Leu Val Ser Phe Leu Ser Leu Gly Thr Phe Phe Gly Ala Leu Thr
145                 150                 155                 160

Ala Pro Phe Ile Ser Asp Ser Tyr Gly Arg Lys Pro Thr Ile Ile Phe
                165                 170                 175

Ser Thr Ile Phe Ile Phe Ser Ile Gly Asn Ser Leu Gln Val Gly Ala
            180                 185                 190

Gly Gly Ile Thr Leu Leu Ile Val Gly Arg Val Ile Ser Gly Ile Gly
        195                 200                 205

Ile Gly Ala Ile Ser Ala Val Val Pro Leu Tyr Gln Ala Glu Ala Thr
    210                 215                 220

His Lys Ser Leu Arg Gly Ala Ile Ile Ser Thr Tyr Gln Trp Ala Ile
225                 230                 235                 240

Thr Trp Gly Leu Leu Val Ser Ser Ala Val Ser Gln Gly Thr His Ala
                245                 250                 255

Arg Asn Asp Ala Ser Ser Tyr Arg Ile Pro Ile Gly Leu Gln Tyr Val
```

-continued

```
                260                 265                 270
Trp Ser Ser Phe Leu Ala Ile Gly Met Phe Leu Pro Glu Ser Pro
        275                 280                 285
Arg Tyr Tyr Val Leu Lys Asp Lys Leu Asp Glu Ala Ala Lys Ser Leu
290                 295                 300
Ser Phe Leu Arg Gly Val Pro Val His Asp Ser Gly Leu Leu Glu Glu
305                 310                 315                 320
Leu Val Glu Ile Lys Ala Thr Tyr Asp Tyr Glu Ala Ser Phe Gly Ser
                325                 330                 335
Ser Asn Phe Ile Asp Cys Phe Ile Ser Ser Lys Ser Arg Pro Lys Gln
                340                 345                 350
Thr Leu Arg Met Phe Thr Gly Ile Ala Leu Gln Ala Phe Gln Gln Phe
                355                 360                 365
Ser Gly Ile Asn Phe Ile Phe Tyr Tyr Gly Val Asn Phe Phe Asn Lys
                370                 375                 380
Thr Gly Val Ser Asn Ser Tyr Leu Val Ser Phe Ile Thr Tyr Ala Val
385                 390                 395                 400
Asn Val Val Phe Asn Val Pro Gly Leu Phe Phe Val Glu Phe Phe Gly
                405                 410                 415
Arg Arg Lys Val Leu Val Val Gly Gly Val Ile Met Thr Ile Ala Asn
                420                 425                 430
Phe Ile Val Ala Ile Val Gly Cys Ser Leu Lys Thr Val Ala Ala Ala
                435                 440                 445
Lys Val Met Ile Ala Phe Ile Cys Leu Phe Ile Ala Ala Phe Ser Ala
                450                 455                 460
Thr Trp Gly Gly Val Val Trp Val Ile Ser Ala Glu Leu Tyr Pro Leu
465                 470                 475                 480
Gly Val Arg Ser Lys Cys Thr Ala Ile Cys Ala Ala Ala Asn Trp Leu
                485                 490                 495
Val Asn Phe Ile Cys Ala Leu Ile Thr Pro Tyr Ile Val Asp Thr Gly
                500                 505                 510
Ser His Thr Ser Ser Leu Gly Ala Lys Ile Phe Phe Ile Trp Gly Ser
                515                 520                 525
Leu Asn Ala Met Gly Val Ile Val Val Tyr Leu Thr Val Tyr Glu Thr
                530                 535                 540
Lys Gly Leu Thr Leu Glu Glu Ile Asp Glu Leu Tyr Ile Lys Ser Ser
545                 550                 555                 560
Thr Gly Val Val Ser Pro Lys Phe Asn Lys Asp Ile Arg Glu Arg Ala
                565                 570                 575
Leu Lys Phe Gln Tyr Asp Pro Leu Gln Arg Leu Glu Asp Gly Lys Asn
                580                 585                 590
Thr Phe Val Ala Lys Arg Asn Asn Phe Asp Asp Glu Thr Pro Arg Asn
                595                 600                 605
Asp Phe Arg Asn Thr Ile Ser Gly Glu Ile Asp His Ser Pro Asn Gln
                610                 615                 620
Lys Glu Val His Ser Ile Pro Glu Arg Val Asp Ile Pro Thr Ser Thr
625                 630                 635                 640
Glu Ile Leu Glu Ser Pro Asn Lys Ser Ser Gly Met Thr Val Pro Val
                645                 650                 655
Ser Pro Ser Leu Gln Asp Val Pro Ile Pro Gln Thr Thr Glu Pro Ala
                660                 665                 670
Glu Ile Arg Thr Lys Tyr Val Asp Leu Gly Asn Gly Leu Gly Leu Asn
                675                 680                 685
```

-continued

Thr Tyr Asn Arg Gly Pro Pro Ser Leu Ser Ser Asp Ser Glu Asp
690                 695                 700

Tyr Thr Glu Asp Glu Ile Gly Gly Pro Ser Ser Gln Gly Asp Gln Ser
705                 710                 715                 720

Asn Arg Ser Thr Met Asn Asp Ile Asn Asp Tyr Met Ala Arg Leu Ile
            725                 730                 735

His Ser Thr Ser Thr Ala Ser Asn Thr Thr Asp Lys Phe Ser Gly Asn
            740                 745                 750

Gln Ser Thr Leu Arg Tyr His Thr Ala Ser Ser His Ser Asp Thr Thr
        755                 760                 765

Glu Glu Asp Ser Asn Leu Met Asp Leu Gly Asn Gly Leu Ala Leu Asn
770                 775                 780

Ala Tyr Asn Arg Gly Pro Pro Ser Ile Leu Met Asn Ser Ser Asp Glu
785                 790                 795                 800

Glu Ala Asn Gly Gly Glu Thr Ser Asp Asn Leu Asn Thr Ala Gln Asp
            805                 810                 815

Leu Ala Gly Met Lys Glu Arg Met Ala Gln Phe Ala Gln Ser Tyr Ile
            820                 825                 830

Asp Lys Arg Gly Gly Leu Glu Pro Glu Thr Gln Ser Asn Ile Leu Ser
        835                 840                 845

Thr Ser Leu Ser Val Met Ala Asp Thr Asn Glu His Asn Asn Glu Ile
850                 855                 860

Leu His Ser Ser Glu Glu Asn Ala Thr Asn Gln Pro Val Asn Glu Asn
865                 870                 875                 880

Asn Asp Leu Lys

<210> SEQ ID NO 3
<211> LENGTH: 763
<212> TYPE: PRT
<213> ORGANISM: Saccharomyces cerevisiae

<400> SEQUENCE: 3

Met Asn Asp Ser Gln Asn Cys Leu Arg Gln Arg Glu Glu Asn Ser His
1               5                   10                  15

Leu Asn Pro Gly Asn Asp Phe Gly His His Gln Gly Ala Glu Cys Thr
            20                  25                  30

Ile Asn His Asn Asn Met Pro His Arg Asn Ala Tyr Thr Glu Ser Thr
        35                  40                  45

Asn Asp Thr Glu Ala Lys Ser Ile Val Met Cys Asp Asp Pro Asn Ala
50                  55                  60

Tyr Gln Ile Ser Tyr Thr Asn Asn Glu Pro Ala Gly Asp Gly Ala Ile
65                  70                  75                  80

Glu Thr Thr Ser Ile Leu Leu Ser Gln Pro Leu Pro Leu Arg Ser Asn
            85                  90                  95

Val Met Ser Val Leu Val Gly Ile Phe Val Ala Val Gly Gly Phe Leu
            100                 105                 110

Phe Gly Tyr Asp Thr Gly Leu Ile Asn Ser Ile Thr Asp Met Pro Tyr
        115                 120                 125

Val Lys Thr Tyr Ile Ala Pro Asn His Ser Tyr Phe Thr Thr Ser Gln
130                 135                 140

Ile Ala Ile Leu Val Ser Phe Leu Ser Leu Gly Thr Phe Phe Gly Ala
145                 150                 155                 160

Leu Ile Ala Pro Tyr Ile Ser Asp Ser Tyr Gly Arg Lys Pro Thr Ile
            165                 170                 175

-continued

```
Met Phe Ser Thr Ala Val Ile Phe Ser Ile Gly Asn Ser Leu Gln Val
            180                 185                 190

Ala Ser Gly Gly Leu Val Leu Leu Ile Val Gly Arg Val Ile Ser Gly
            195                 200                 205

Ile Gly Ile Gly Ile Ile Ser Ala Val Val Pro Leu Tyr Gln Ala Glu
            210                 215                 220

Ala Ala Gln Lys Asn Leu Arg Gly Ala Ile Ile Ser Ser Tyr Gln Trp
225                 230                 235                 240

Ala Ile Thr Ile Gly Leu Leu Val Ser Ser Ala Val Ser Gln Gly Thr
                245                 250                 255

His Ser Lys Asn Gly Pro Ser Ser Tyr Arg Ile Pro Ile Gly Leu Gln
            260                 265                 270

Tyr Val Trp Ser Ser Ile Leu Ala Val Gly Met Ile Phe Leu Pro Glu
            275                 280                 285

Ser Pro Arg Tyr Tyr Val Leu Lys Asp Glu Leu Asn Lys Ala Ala Lys
            290                 295                 300

Ser Leu Ser Phe Leu Arg Gly Leu Pro Ile Glu Asp Pro Arg Leu Leu
305                 310                 315                 320

Glu Glu Leu Val Glu Ile Lys Ala Thr Tyr Asp Tyr Glu Ala Ser Phe
                325                 330                 335

Gly Pro Ser Thr Leu Leu Asp Cys Phe Lys Thr Ser Glu Asn Arg Pro
            340                 345                 350

Lys Gln Ile Leu Arg Ile Phe Thr Gly Ile Ala Ile Gln Ala Phe Gln
            355                 360                 365

Gln Ala Ser Gly Ile Asn Phe Ile Phe Tyr Tyr Gly Val Asn Phe Phe
            370                 375                 380

Asn Asn Thr Gly Val Asp Asn Ser Tyr Leu Val Ser Phe Ile Ser Tyr
385                 390                 395                 400

Ala Val Asn Val Ala Phe Ser Ile Pro Gly Met Tyr Leu Val Asp Arg
                405                 410                 415

Ile Gly Arg Arg Pro Val Leu Leu Ala Gly Gly Val Ile Met Ala Ile
            420                 425                 430

Ala Asn Leu Val Ile Ala Ile Val Gly Val Ser Glu Gly Lys Thr Val
            435                 440                 445

Val Ala Ser Lys Ile Met Ile Ala Phe Ile Cys Leu Phe Ile Ala Ala
            450                 455                 460

Phe Ser Ala Thr Trp Gly Gly Val Val Trp Val Val Ser Ala Glu Leu
465                 470                 475                 480

Tyr Pro Leu Gly Val Arg Ser Lys Cys Thr Ala Ile Cys Ala Ala Ala
                485                 490                 495

Asn Trp Leu Val Asn Phe Thr Cys Ala Leu Ile Thr Pro Tyr Ile Val
            500                 505                 510

Asp Val Gly Ser His Thr Ser Ser Met Gly Pro Lys Ile Phe Phe Ile
            515                 520                 525

Trp Gly Gly Leu Asn Val Val Ala Val Ile Val Val Tyr Phe Ala Val
            530                 535                 540

Tyr Glu Thr Arg Gly Leu Thr Leu Glu Glu Ile Asp Glu Leu Phe Arg
545                 550                 555                 560

Lys Ala Pro Asn Ser Val Ile Ser Ser Lys Trp Asn Lys Lys Ile Arg
                565                 570                 575

Lys Arg Cys Leu Ala Phe Pro Ile Ser Gln Gln Ile Glu Met Lys Thr
            580                 585                 590
```

```
Asn Ile Lys Asn Ala Gly Lys Leu Asp Asn Asn Ser Pro Ile Val
            595                 600                 605

Gln Asp Asp Ser His Asn Ile Ile Asp Val Gly Phe Leu Glu Asn
610                 615                 620

Gln Ile Gln Ser Asn Asp His Met Ile Ala Ala Asp Lys Gly Ser Gly
625                 630                 635                 640

Ser Leu Val Asn Ile Ile Asp Thr Ala Pro Leu Thr Ser Thr Glu Phe
                645                 650                 655

Lys Pro Val Glu His Pro Pro Val Asn Tyr Val Asp Leu Gly Asn Gly
                660                 665                 670

Leu Gly Leu Asn Thr Tyr Asn Arg Gly Pro Ser Ile Ile Ser Asp
            675                 680                 685

Ser Thr Asp Glu Phe Tyr Glu Glu Asn Asp Ser Ser Tyr Tyr Asn Asn
690                 695                 700

Asn Thr Glu Arg Asn Gly Ala Asn Ser Val Asn Thr Tyr Met Ala Gln
705                 710                 715                 720

Leu Ile Asn Ser Ser Thr Thr Ser Asn Asp Thr Ser Phe Ser Pro
            725                 730                 735

Ser His Asn Ser Asn Ala Arg Thr Ser Ser Asn Trp Thr Ser Asp Leu
                740                 745                 750

Ala Ser Lys His Ser Gln Tyr Thr Ser Pro Gln
            755                 760

<210> SEQ ID NO 4
<211> LENGTH: 961
<212> TYPE: PRT
<213> ORGANISM: Saccharomyces cerevisiae

<400> SEQUENCE: 4

Met Ile Thr Glu Gly Phe Pro Pro Asn Leu Asn Ala Leu Lys Gly Ser
1               5                   10                  15

Ser Leu Leu Glu Lys Arg Val Asp Ser Leu Arg Gln Leu Asn Thr Thr
                20                  25                  30

Thr Val Asn Gln Leu Leu Gly Leu Pro Gly Met Thr Ser Thr Phe Thr
            35                  40                  45

Ala Pro Gln Leu Leu Gln Leu Arg Ile Ile Ala Ile Thr Ala Ser Ala
50                  55                  60

Val Ser Leu Ile Ala Gly Cys Leu Gly Met Phe Phe Leu Ser Lys Met
65                  70                  75                  80

Asp Lys Arg Arg Lys Val Phe Arg His Asp Leu Ile Ala Phe Leu Ile
                85                  90                  95

Ile Cys Asp Phe Leu Lys Ala Phe Ile Leu Met Ile Tyr Pro Met Ile
                100                 105                 110

Ile Leu Ile Asn Asn Ser Val Tyr Ala Thr Pro Ala Phe Phe Asn Thr
            115                 120                 125

Leu Gly Trp Phe Thr Ala Phe Ala Ile Glu Gly Ala Asp Met Ala Ile
130                 135                 140

Met Ile Phe Ala Ile His Phe Ala Leu Ile Phe Lys Pro Asn Trp
145                 150                 155                 160

Lys Trp Arg Asn Lys Arg Ser Gly Asn Met Glu Gly Gly Leu Tyr Lys
                165                 170                 175

Lys Arg Ser Tyr Ile Trp Pro Ile Thr Ala Leu Val Pro Ala Ile Leu
            180                 185                 190

Ala Ser Leu Ala Phe Ile Asn Tyr Asn Lys Leu Asn Asp Asp Ser Asp
            195                 200                 205
```

```
Thr Thr Ile Ile Leu Asp Asn Asn Tyr Asn Phe Pro Asp Ser Pro
    210                 215                 220

Arg Gln Gly Gly Tyr Lys Pro Trp Ser Ala Trp Cys Tyr Leu Pro Pro
225                 230                 235                 240

Lys Pro Tyr Trp Tyr Lys Ile Val Leu Ser Trp Gly Pro Arg Tyr Phe
                245                 250                 255

Ile Ile Ile Phe Ile Phe Ala Val Tyr Leu Ser Ile Tyr Ile Phe Ile
                260                 265                 270

Thr Ser Glu Ser Lys Arg Ile Lys Ala Gln Ile Gly Asp Phe Asn His
            275                 280                 285

Asn Val Leu Glu Glu Glu Lys Glu Lys Lys Leu Phe Gly Leu Gly
            290                 295                 300

His Trp Gly Lys Ala Lys Trp Tyr Phe Arg Ser Tyr Phe Lys Leu Pro
305                 310                 315                 320

Leu Leu His Leu Leu Arg Asn Leu Lys Asn Phe Phe Thr Ile Ser Phe
                325                 330                 335

Ile Asp Pro Asn Glu Glu Thr Asp Asp Ser Gly Ser Ser Asn Gly Thr
            340                 345                 350

Phe Asn Phe Gly Glu Ser Ser Asn Glu Ile Pro Thr Leu Phe Arg Lys
            355                 360                 365

Thr Asn Thr Gly Ser Asp Glu Asn Val Ser Ala Ser Gly Gly Val Arg
370                 375                 380

Leu Leu Asp Tyr Asn Ser Ala Lys Pro Leu Asp Met Ser Lys Tyr Ala
385                 390                 395                 400

Met Ser Glu Gln Pro Asp Leu Glu Arg Asn Asn Pro Phe Asp Cys Glu
                405                 410                 415

Asn Asp Ile Thr Leu Asn Pro Ser Glu Leu Val Ser Lys Gln Lys Glu
            420                 425                 430

His Lys Val Thr Phe Ser Val Glu Asn Glu Gly Leu Asp Thr Arg Lys
            435                 440                 445

Ser Ser Met Leu Gly His Gln Thr Phe Ser Cys Gln Asn Ser Leu Glu
450                 455                 460

Ser Pro Leu Ala Met Tyr Asp Asn Lys Asn Asp Asn Ser Asp Ile Thr
465                 470                 475                 480

Ser Asn Ile Lys Glu Lys Gly Gly Ile Ile Asn Asn Asn Ser Asn Asn
                485                 490                 495

Asp Asp Asp Asp Asn Asn Asn Asn Asp Asn Asp Asn Asp Asn Asn
                500                 505                 510

Asn Ser Asn Asn Asn Asn Asn Asn Asn Asn Asn Asn Asn Asn Asn
            515                 520                 525

Asn Asn Asn Asn Asn Asn Asn Asn Asn Asn Asn Asn
530                 535                 540

Ser Asn Asn Ile Lys Asn Asn Val Asp Asn Asn Thr Asn Pro Ala
545                 550                 555                 560

Asp Asn Ile Pro Thr Leu Ser Asn Glu Ala Phe Thr Pro Ser Gln Gln
                565                 570                 575

Phe Ser Gln Glu Arg Val Asn Asn Ala Asp Arg Cys Glu Asn Ser
                580                 585                 590

Ser Phe Thr Asn Val Gln Gln His Phe Gln Ala Gln Thr Tyr Lys Gln
            595                 600                 605

Met Lys Lys Arg Arg Ala Gln Ile Gln Lys Asn Leu Arg Ala Ile Phe
610                 615                 620
```

```
Ile Tyr Pro Leu Ser Tyr Ile Gly Ile Trp Leu Phe Pro Ile Ile Ala
625                 630                 635                 640

Asp Ala Leu Gln Tyr Asn His Glu Ile Lys His Gly Pro Thr Met Trp
                645                 650                 655

Val Thr Tyr Ile Asp Thr Cys Val Arg Pro Leu Ser Cys Leu Val Asp
            660                 665                 670

Val Ile Val Tyr Leu Phe Lys Glu Lys Pro Trp Asn Tyr Ser Trp Ala
        675                 680                 685

Lys Thr Glu Ser Lys Tyr Leu Ile Glu Lys Tyr Ile Leu Lys Gly Glu
        690                 695                 700

Leu Gly Glu Lys Glu Ile Leu Lys Phe Cys His Ser Asn Trp Gly Lys
705                 710                 715                 720

Arg Gly Trp Tyr Tyr Arg Gly Lys Trp Lys Lys Arg Lys Cys Trp Lys
                725                 730                 735

Tyr Ser Thr Asn Pro Leu Lys Arg Ile Leu Trp Phe Val Glu Arg Phe
                740                 745                 750

Phe Lys Gln Leu Phe Glu Leu Lys Leu His Phe Ser Phe Tyr Asp Asn
            755                 760                 765

Cys Asp Asp Phe Glu Tyr Trp Glu Asn Tyr Tyr Ser Ala Lys Asp Ser
770                 775                 780

Asn Asp Asn Lys Arg Thr Glu Ser Asp Glu Thr Lys Thr Asn Ser Ser
785                 790                 795                 800

Asp Arg Ser Leu Pro Ser Asn Ser Leu Glu Leu Gln Ala Met Leu Asn
                805                 810                 815

Asn Ile Thr Ala Glu Glu Val Glu Val Pro Leu Phe Trp Arg Ile Ile
            820                 825                 830

His His Ile Pro Met Leu Gly Gly Ile Asp Leu Asp Glu Leu Asn Arg
            835                 840                 845

Leu Leu Lys Ile Arg Tyr Asn Asn Asp His Phe Ser Leu Pro Gly Leu
850                 855                 860

Lys Phe Ala Leu Asn Gln Asn Lys Ser His Asp Lys His Gln Asp Val
865                 870                 875                 880

Ser Thr Asn Ser Met Val Lys Ser Ser Phe Phe Ser Ser Asn Ile Val
                885                 890                 895

Thr Asn Asp Asp Glu Asn Ser Ile Glu Glu Asp Lys Asn Leu Arg Tyr
            900                 905                 910

Ser Asp Ala Ser Ala Ser Glu Asn Tyr Leu Val Lys Pro Thr Ile Pro
        915                 920                 925

Gly Thr Thr Pro Asp Pro Ile Ile Glu Ala Gln Asn Asp Asn Asp Ser
930                 935                 940

Ser Asp Ser Ser Gly Ile Asp Leu Ile Ala Phe Leu Arg Asn Gly Pro
945                 950                 955                 960

Leu
```